(12) United States Patent
Shah et al.

(10) Patent No.: US 12,227,812 B2
(45) Date of Patent: Feb. 18, 2025

(54) COMPOSITIONS AND METHODS FOR DETECTING NUCLEIC ACIDS OF EPSTEIN-BARR VIRUS

(71) Applicant: GEN-PROBE INCORPORATED, San Diego, CA (US)

(72) Inventors: Ankur Shah, San Diego, CA (US); Jian Yu Fung, Chino Hills, CA (US)

(73) Assignee: Gen-Probe Incorporated, San Diego, CA (US)

( * ) Notice: Subject to any disclaimer, the term of this patent is extended or adjusted under 35 U.S.C. 154(b) by 1010 days.

(21) Appl. No.: 17/264,574

(22) PCT Filed: Aug. 1, 2019

(86) PCT No.: PCT/US2019/044614
§ 371 (c)(1),
(2) Date: Jan. 29, 2021

(87) PCT Pub. No.: WO2020/028631
PCT Pub. Date: Feb. 6, 2020

(65) Prior Publication Data
US 2021/0332449 A1    Oct. 28, 2021

Related U.S. Application Data

(60) Provisional application No. 62/713,330, filed on Aug. 1, 2018.

(51) Int. Cl.
*C12Q 1/70* (2006.01)
(52) U.S. Cl.
CPC ....... *C12Q 1/705* (2013.01); *C12Q 2600/158* (2013.01)
(58) Field of Classification Search
CPC ................ C12Q 1/705; C12Q 2600/158
See application file for complete search history.

(56) References Cited

U.S. PATENT DOCUMENTS

| 2003/0124530 A1* | 7/2003 | Edwards | ............... C12Q 1/701 |
| | | | 435/6.13 |
| 2004/0005551 A1 | 1/2004 | Lo et al. | |
| 2016/0251724 A1* | 9/2016 | Ng | .......... C12Q 1/705 |
| | | | 435/5 |

FOREIGN PATENT DOCUMENTS

| JP | 5-309000 A | 11/1993 |
| JP | 7-79776 A | 3/1995 |
| JP | 11-137300 | 5/1999 |
| JP | 2001511120 A | 8/2001 |
| JP | 2002505122 A | 2/2002 |
| JP | 2007325514 A | 12/2007 |
| WO | 199830586 A2 | 7/1998 |
| WO | 199945155 A2 | 9/1999 |

OTHER PUBLICATIONS

Incomserb et al. "Establishment of Real-Time Polymerase Chain Reaction-Based Assay for Quantitation of Epstein-Barr Virus DNA in Healthy Donors and in Patients with EBV Associated Lymphoma," The Journal of the Medical Association of Thailand, 88(Supl 4); S280-S286 (2005).
PCT, International Search Report and Written Opinion for Application No. PCT/US2019/044614, mailed Sep. 10, 2029, 12 pages.

* cited by examiner

Primary Examiner — Neil P Hammell
Assistant Examiner — Kelly Nichet Hassell
(74) Attorney, Agent, or Firm — Michael J. Gilly; Adam M. Breier

(57) ABSTRACT

Disclosed are compositions, methods, and kits that can be used to Epstein-Ban virus (EBV) in a sample undergoing testing. Nucleic acids of EBV can be isolated, amplified and detected with specificity by real-time PCR, and without interference from non-EBV organisms. In some embodiments, nucleic acids used for amplification are isolated from human blood, or blood products. Nucleic acid isolation, amplification and detection steps can all be carried out using an automated instrument.

44 Claims, No Drawings

Specification includes a Sequence Listing.

COMPOSITIONS AND METHODS FOR DETECTING NUCLEIC ACIDS OF EPSTEIN-BARR VIRUS

RELATED APPLICATIONS

This application is a national phase entry pursuant to 35 U.S.C. § 371 of International Application No. PCT/US2019/044614, filed Aug. 1, 2019, which claims the benefit of U.S. Provisional Application No. 62/713,330, filed Aug. 1, 2018. The entire disclosures of these prior applications are hereby incorporated by reference.

TECHNICAL FIELD

The present disclosure generally relates to the field of biotechnology. More particularly, the disclosure relates to molecular diagnostic assays for detecting Epstein Barr virus (EBV).

BACKGROUND

Epstein-Barr virus ("EBV") is one of eight known human herpesvirus types in the herpes family, and is one of the most common viruses in humans This virus, also known as human herpesvirus 4, is found all over the world. Most people are infected with EBV at some point in their lives. The virus spreads most commonly through bodily fluids (e.g., saliva), and is the cause of infectious mononucleosis. In addition, EBV has been implicated in several other diseases, including: Burkitt's lymphoma; Hodgkin's lymphoma; stomach cancer; nasopharyngeal carcinoma; multiple sclerosis; lymphomatoid granulomatosis; and more.

Symptoms of EBV infection differ by age of the infected individual. Infections during childhood may not cause symptoms, or may cause symptoms that are not distinguishable from other mild, brief childhood illnesses. Symptoms in teenagers and adults usually resolve in two to four weeks, but are more pronounced and can include: fatigue, fever, inflamed throat, swollen lymph nodes in the neck, enlarged spleen, and a rash. The virus can remain latent (inactive) in B-cells, but can be reactivated to result in an infectious condition. Since the symptoms of EBV infection can be similar to other illnesses, examining blood for anti-EBV antibodies has been used for improved diagnostic testing.

EBV can infect both B cells and epithelial cells. The virus has a double-stranded DNA genome of about 172 kb that is organized into 85 genes. The DNA genome of the EBV virion is surrounded by a protein nucleocapsid, which is in turn surrounded by a tegument made of protein, and in turn surrounded by a lipid envelope containing lipids and surface glycoproteins (envelope proteins). Lytic replication (productive infection) of the virus requires linearization of the genome, which then is replicated by a virally encoded DNA polymerase. During latency, when the EBV genome has a circular conformation, DNA polymerase of the host cell is responsible for replication.

Given the range of symptoms, and the fact that symptoms can differ at different stages of life, there is a need for a simplified and accurate approach for identifying EBV infection. Unfortunately, EBV is one among several viruses that are closely related at the nucleic acid sequence level. The challenge, therefore, is to be able to detect EBV in a specific and sensitive fashion without detecting any other herpesvirus target nucleic acid, and without detecting human nucleic acid. The present disclosure addresses this point.

SUMMARY

In one aspect, the disclosure concerns a reaction mixture useful for determining the presence or absence of Epstein-Barr virus (EBV) in a sample. Generally speaking, the reaction mixture includes a detection probe oligomer for detecting EBV nucleic acids, where the detection probe oligomer is up to 30 nucleotides in length and includes the base sequence of SEQ ID NO:22 or the complement thereof, allowing for substitution of RNA and DNA equivalent bases. Also included in the reaction mixture is a pair of amplification oligomers, where a first amplification oligomer of the pair includes 18-25 contiguous bases of SEQ ID NO:3, allowing for substitution of RNA and DNA equivalent bases, and where a second amplification oligomer of the pair includes 18-25 contiguous bases of SEQ ID NO:4, allowing for substitution of RNA and DNA equivalent bases. In some embodiments, the detection probe oligomer further includes a detectable label. The detectable label can include an interactive label pair including a fluorophore moiety and a quencher moiety. In some embodiments, the detection probe oligomer further includes at least one nucleotide analog. The at least one nucleotide analog of the detection probe oligomer can include at least one 5-methyl cytosine base. In some embodiments, the detection probe oligomer is 22 nucleotides in length and includes the base sequence of SEQ ID NO:9. In some embodiments, each of the first and second amplification oligomers is up to 25 nucleotides in length. In some embodiments, the first amplification oligomer is 20 nucleotides in length, and the base sequence of the first amplification oligomer consists of 20 contiguous bases of SEQ ID NO:3. In some embodiments, the base sequence of the first amplification oligomer is SEQ ID NO:5. In some embodiments, the second amplification oligomer is 20 nucleotides in length, and the base sequence of the second amplification oligomer consists of 20 contiguous bases of SEQ ID NO:4. In some embodiments, the base sequence of the second amplification oligomer is SEQ ID NO:7. In some embodiments, the base sequence of the first amplification oligomer is either SEQ ID NO:5 or SEQ ID NO:6, and the base sequence of the second amplification oligomer is either SEQ ID NO:7 or SEQ ID NO:8. In some embodiments, the base sequence of the first amplification oligomer is SEQ ID NO:5. In some embodiments, the base sequence of the second amplification oligomer is SEQ ID NO:7. In some embodiments the base sequence of the second amplification oligomer is SEQ ID NO:7.

In another aspect, the disclosure concerns a method of determining the presence or absence of Epstein-Barr virus (EBV) in a sample. The method includes the step of (a) contacting a sample to be tested for the presence of EBV with an oligomer combination that includes: a first amplification oligomer that includes 18-25 contiguous bases of SEQ ID NO:3, allowing for substitution of RNA and DNA equivalent bases; a second amplification oligomer that includes 18-25 contiguous bases of SEQ ID NO:4, allowing for substitution of RNA and DNA equivalent bases; and a detection probe oligomer of up to 30 nucleotides in length that includes the base sequence of SEQ ID NO:22 or the complement thereof, allowing for substitution of RNA and DNA equivalent bases. There also is the step of (b) performing an in vitro nucleic acid amplification reaction using the oligomer combination, where any EBV target nucleic acid, if present in the sample, is a template for generating an amplification product. There also is the step of (c) detecting, with the detection probe oligomer, the presence or absence of the amplification product, thereby determining the presence or absence of EBV in the sample. In some embodiments, the detection probe oligomer further includes a detectable label. The detectable label of the detection probe oligomer can include an interactive label pair that includes a fluorophore moiety and a quencher moiety. In some embodiments, the detection probe oligomer further includes at least one nucleotide analog. The at least one nucleotide analog can include at least one 5-methyl cytosine base. In some embodiments, the detection probe oligomer is 22 nucleotides in length and includes the base sequence of SEQ ID NO:9. In some embodiments, the sample includes nucleic acids isolated from any of human blood, human plasma, or human serum. In some embodiments, the in vitro nucleic acid amplification reaction includes Taq DNA polymerase. In some embodiments, steps (b) and (c) take place concurrently, and the in vitro nucleic acid amplification reaction is a real-time nucleic acid amplification reaction. In some embodiments, the in vitro nucleic acid amplification reaction in step (b) is a multiplex in vitro nucleic acid amplification reaction that amplifies and detects, in addition to any nucleic acid of EBV that may be present in the sample, any nucleic acid of cytomegalovirus (CMV) that may be present in the sample. In some embodiments, the in vitro nucleic acid amplification reaction in step (b) is a PCR amplification reaction that includes a DNA polymerase with a 5' to 3' exonuclease activity. In some embodiments, before step (a) there is the step of isolating nucleic acids, and where all of the steps are performed using a single automated instrument.

In another aspect, the disclosure concerns a kit of reagents. The kit includes, in one or more vials: a detection probe oligomer for detecting Epstein-Barr virus (EBV) nucleic acids, where the detection probe oligomer is up to 30 nucleotides in length and includes the base sequence of SEQ ID NO:22 or the complement thereof, allowing for substitution of RNA and DNA equivalent bases; and a pair of amplification oligomers. A first amplification oligomer of the pair includes 18-25 contiguous bases of SEQ ID NO:3, allowing for substitution of RNA and DNA equivalent bases. A second amplification oligomer of the pair includes 18-25 contiguous bases of SEQ ID NO:4, allowing for substitution of RNA and DNA equivalent bases. In some embodiments, the detection probe oligomer further includes a detectable label. The detectable label of the detection probe oligomer can include an interactive label pair that includes a fluorophore moiety and a quencher moiety. In some embodiments, the detection probe oligomer further includes at least one nucleotide analog. The at least one nucleotide analog of the detection probe oligomer can include at least one 5-methyl cytosine base. In some embodiments, the detection probe oligomer is 22 nucleotides in length and includes the base sequence of SEQ ID NO:9. In some embodiments, each of the first and second amplification oligomers is up to 25 nucleotides in length. In some embodiments, the first amplification oligomer is 20 nucleotides in length, and the base sequence of the first amplification oligomer consists of 20 contiguous bases of SEQ ID NO:3. In some embodiments, the base sequence of the first amplification oligomer is SEQ ID NO:5. In some embodiments, the second amplification oligomer is 20 nucleotides in length, and the base sequence of the second amplification oligomer consists of 20 contiguous bases of SEQ ID NO:4. In some embodiments, the base sequence of the second amplification oligomer is SEQ ID NO:7. In some embodiments, the base sequence of the first amplification oligomer is either SEQ ID NO:5 or SEQ ID NO:6, and the base sequence of the second amplification oligomer is either SEQ ID NO:7 or SEQ ID NO:8. In some embodiments, the base sequence of the first amplification oligomer is SEQ ID NO:5. In some embodiments, the base sequence of the second amplification oligomer is SEQ ID NO:7. In some embodiments, the base sequence of the second amplification oligomer is SEQ ID NO:7. In some embodiments, the first and second amplification oligomers are packaged together in one vial, and the probe oligonucleotide is packaged in a separate vial.

In another aspect, the disclosure concerns a detection probe oligomer for detecting Epstein-Barr virus (EBV) nucleic acids. The detection probe oligomer is up to 30 nucleotides in length and includes the base sequence of SEQ ID NO:22 or the complement thereof, allowing for substitution of RNA and DNA equivalent bases. In some embodiments, the detection probe oligomer further includes a detectable label. The detectable label can include an interactive label pair that includes a fluorophore moiety and a quencher moiety. In some embodiments, the detection probe oligomer further includes at least one nucleotide analog. The at least one nucleotide analog can include at least one 5-methyl cytosine base. In some embodiments, the detection probe oligomer is up to 26 nucleotides in length and includes a base sequence fully contained within the sequence of SEQ ID NO:17 or the complement thereof. In some embodiments, the detection probe oligomer is up to 22 nucleotides in length. In some embodiments, the detection probe oligomer is 22 nucleotides in length and includes the base sequence of SEQ ID NO:9 or the complement thereof. In some embodiments, the detection probe oligomer is 22 nucleotides in length and includes the base sequence of SEQ ID NO:9. In some embodiments, the detection probe oligomer further includes at least nine nucleotide analogs. In some embodiments, the detection probe oligomer further includes nine 5-methyl cytosine nucleotide analogs. In some embodiments, the detection probe oligomer is 22 nucleotides in length with a base sequence consisting of SEQ ID NO:9. In some embodiments, the detection probe oligomer includes a plurality of 5-methyl cytosine nucleotide analogs. In some embodiments, every cytosine base in the sequence of SEQ ID NO:9 is the 5-methyl cytosine nucleotide analog. In some embodiments, the detection probe oligomer is a dual-labeled hydrolysis probe. In some embodiments, the probe is hybridized to a complementary nucleic acid strand in the presence of a DNA polymerase that includes a 5' to 3' exonuclease activity.

Definitions

Unless defined otherwise, all technical and scientific terms used herein have the same meaning as commonly understood by one of ordinary skill in the art pertinent to the methods and compositions described. General definitions may be found in technical books relevant to the art of molecular biology (e.g., Dictionary of Microbiology and Molecular Biology, 2nd ed., Singleton et al., 1994, John Wiley & Sons, New York, NY; or The Harper Collins Dictionary of Biology, Hale & Marham, 1991, Harper Perennial, New York, NY). As used herein, the following terms and phrases have the meanings ascribed to them unless specified otherwise.

The terms "a," "an," and "the" include plural referents, unless the context clearly indicates otherwise. For example, "a nucleic acid" as used herein is understood to represent one or more nucleic acids. As such, the terms "a" (or "an"), "one or more," and "at least one" can be used interchangeably herein.

It will be appreciated that there is an implied "about" prior to the temperatures, concentrations, and times discussed in the present disclosure, such that slight and insubstantial deviations are within the scope of the present teachings. In general, the term "about" indicates insubstantial variation in a quantity of a component of a composition not having any significant effect on the activity or stability of the composition. All ranges are to be interpreted as encompassing the endpoints in the absence of express exclusions such as "not including the endpoints"; thus, for example, "within 10-15" includes the values 10 and 15. Also, the use of "comprise," "comprises," "comprising," "contain," "contains," "containing," "include," "includes," and "including" are not intended to be limiting. It is to be understood that both the foregoing general description and detailed description are exemplary and explanatory only and are not restrictive of the teachings. To the extent that any material incorporated by reference is inconsistent with the express content of this disclosure, the express content controls.

Unless specifically noted, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims). "Consisting essentially of" means that additional component(s), composition(s) or method step(s) that do not materially change the basic and novel characteristics of the compositions and methods described herein may be included in those compositions or methods. Such characteristics include the ability to detect an Epstein-Barr virus (EBV) nucleic acid sequence present in a sample with specificity that distinguishes the EBV nucleic acid from other known pathogens (e.g., CMV), optionally at a sensitivity that can detect the virus present in a sample at a concentration of about 50 copies/ml, and, optionally within about 60 minutes and/or within about 40 cycles from the beginning of an amplification reaction when a cycled amplification reaction is used.

"Sample" includes any specimen that may contain EBV or components thereof, such as nucleic acids or fragments of nucleic acids. Samples include "biological samples" which include any tissue or material derived from a living or dead human that may contain EBV or target nucleic acid derived therefrom, including for example: peripheral blood, plasma, serum, lymph node, vaginal swab samples, cervical brush samples, respiratory tissue or exudates such as bronchoscopy, bronchoalveolar lavage (BAL) or lung biopsy, sputum, saliva, gastrointestinal tissue, feces, urine, semen or other body fluids or materials. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support.

"Nucleic acid" and "polynucleotide" refer to a multimeric compound comprising nucleosides or nucleoside analogs which have nitrogenous heterocyclic bases or base analogs linked together to form a polynucleotide, including conventional RNA, DNA, mixed RNA-DNA, and polymers that are analogs thereof. A nucleic acid "backbone" may be made up of a variety of linkages, including one or more of sugar-phosphodiester linkages, peptide-nucleic acid bonds ("peptide nucleic acids" or PNA; PCT Publication No. WO 95/32305), phosphorothioate linkages, methylphosphonate linkages, or combinations thereof. Sugar moieties of a nucleic acid may be ribose, deoxyribose, or similar compounds with substitutions (e.g., 2' methoxy or 2' halide substitutions). Nitrogenous bases may be conventional bases (A, G, C, T, U), analogs thereof (e.g., inosine or others; see *The Biochemistry of the Nucleic Acids* 5-36, Adams et al., ed., 11$^{th}$ ed., 1992), derivatives of purines or pyrimidines (e.g., N$^4$-methyl deoxyguanosine, deaza- or aza-purines, deaza- or aza-pyrimidines, pyrimidine bases with substituent groups at the 5 or 6 position, purine bases with a substituent at the 2, 6, or 8 positions, 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines; U.S. Pat. No. 5,378,825 and PCT Publication No. WO 93/13121). Nucleic acids may include one or more "abasic" residues where the backbone includes no nitrogenous base for position(s) of the polymer (U.S. Pat. No. 5,585,481). A nucleic acid may comprise only conventional RNA or DNA sugars, bases and linkages, or may include both conventional components and substitutions (e.g., conventional bases with 2' methoxy linkages, or polymers containing both conventional bases and one or more base analogs). Nucleic acid includes "locked nucleic acid" (LNA), an analogue containing one or more LNA nucleotide monomers with a bicyclic furanose unit locked in an RNA mimicking sugar conformation, which enhance hybridization affinity toward complementary RNA and DNA sequences (Vester and Wengel, 2004, *Biochemistry* 43(42): 13233-41). Embodiments of oligomers that may affect stability of a hybridization complex include PNA oligomers, oligomers that include 2'-methoxy or 2'-fluoro substituted RNA, or oligomers that affect the overall charge, charge density, or steric associations of a hybridization complex, including oligomers that contain charged linkages (e.g., phosphorothioates) or neutral groups (e.g., methylphosphonates). 5-methylcytosines may be used in conjunction with any of the foregoing backbones/sugars/linkages including RNA or DNA backbones (or mixtures thereof) unless otherwise indicated. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24, and 25).

A "nucleotide" as used herein is a subunit of a nucleic acid consisting of a phosphate group, a 5-carbon sugar, and a nitrogenous base (also referred to herein as "nucleobase"). The 5-carbon sugar found in RNA is ribose. In DNA, the 5-carbon sugar is 2'-deoxyribose. The term also includes analogs of such subunits, such as a methoxy group at the 2' position of the ribose (also referred to herein as "2'-O-Me" or "2'-methoxy").

By "RNA and DNA equivalents" is meant RNA and DNA molecules having essentially the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence. By "DNA/RNA chimeric" is meant a nucleic acid comprising both DNA and RNA nucleotides. Unless the context clearly dictates otherwise, reference to an EBV nucleic acid includes EBV RNA and DNA equivalents and DNA/RNA chimerics thereof.

By "RNA and DNA equivalent bases" is meant nucleotide bases having the same complementary base pair hybridization properties in RNA and DNA. Here the base uracil can be substituted in place of the base thymine, or vice versa, and so uracil and thymine are RNA and DNA equivalent bases. A polynucleotide base sequence 5' -AGCT-3' that allows for substitution of RNA and DNA equivalent bases would also describe the sequence 5'-AGCU-3'. The differences between RNA and DNA equivalent bases do not contribute to differences in homology because the equivalents have the same degree of complementarity to a particular sequence.

The term, "complement" refers to a nucleic acid molecule that comprises a contiguous nucleic acid sequence that is complementary to a contiguous nucleic acid sequence of another nucleic acid molecule (for standard nucleotides A:T, A:U, C:G). For example, 5'-AACTGUC-3' is the complement of 5'-GACAGTT-3'. Two nucleic acid sequences are "sufficiently complementary" when their respective contiguous nucleic acid sequences are at least 70% complementary.

A "target nucleic acid" as used herein is a nucleic acid comprising a target sequence to be amplified. Target nucleic acids may be DNA or RNA, and may be either single-stranded or double-stranded. The target nucleic acid may include other sequences besides the target sequence, which may not be amplified.

The term "target sequence" as used herein refers to the particular nucleotide sequence of the target nucleic acid that is to be amplified and/or detected. The "target sequence" includes the complexing sequences to which oligonucleotides (e.g., priming oligonucleotides and/or promoter oligonucleotides) complex during an amplification processes (e.g., PCR, TMA). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands.

"Target-hybridizing sequence" or "target-specific sequence" is used herein to refer to the portion of an oligomer that is configured to hybridize with a target nucleic acid sequence. Preferably, the target-hybridizing sequences are configured to specifically hybridize with a target nucleic acid sequence. Target-hybridizing sequences may be 100% complementary to the portion of the target sequence to which they are configured to hybridize, but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality strains within a species, such as would be the case for an oligomer configured to hybridize to variants of EBV. It is understood that other reasons exist for configuring a target-hybridizing sequence to have less than 100% complementarity to a target nucleic acid.

The term "target a sequence," as used herein in reference to a region of EBV nucleic acid, refers to a process whereby an oligonucleotide hybridizes to a target sequence in a manner that allows for amplification and detection as described herein. In one preferred embodiment, the oligonucleotide is complementary with the targeted EBV nucleic acid sequence and contains no mismatches. In another preferred embodiment, the oligonucleotide is complementary but contains 1, 2, 3, 4, or 5 mismatches with the targeted EBV nucleic acid sequence. Preferably, the oligomer specifically hybridizes to the target sequence.

The term "configured to" denotes an actual arrangement of the polynucleotide sequence configuration of a referenced oligonucleotide target-hybridizing sequence. For example, amplification oligomers that are configured to generate a specified amplicon from a target sequence have polynucleotide sequences that hybridize to the target sequence and can be used in an amplification reaction to generate the amplicon. Also as an example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing region of an amplification oligonucleotide, detection probe, or other oligonucleotide is designed to have a polynucleotide sequence that could target a sequence of the referenced EBV target region. Such an oligonucleotide is not limited to targeting that sequence only, but is rather useful as a composition, in a kit, or in a method for targeting an EBV target nucleic acid. The oligonucleotide is designed to function as a component of an assay for amplification and detection of EBV from a sample, and therefore is designed to target EBV in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined.

The term "region," as used herein, refers to a portion of a nucleic acid wherein said portion is smaller than the entire nucleic acid. For example, when the nucleic acid in reference is an oligonucleotide promoter primer, the term "region" may be used refer to the smaller promoter portion. Similarly, and also as example only, when the nucleic acid is an EBV target nucleic acid, the term "region" may be used to refer to a smaller area of the nucleic acid, wherein the smaller area is targeted by one or more oligonucleotides of the present disclosure. As another non-limiting example, when the nucleic acid in reference is an amplicon, the term region may be used to refer to the smaller nucleotide sequence identified for hybridization by the target-hybridizing sequence of a probe.

"Oligomer," "oligonucleotide," or "oligo" refers to a nucleic acid of generally less than 1,000 nucleotides (nt), including those in a size range having a lower limit of about 2 to 5 nucleotides and an upper limit of about 500 to 900 nucleotides. Some particular embodiments are oligomers in a size range with a lower limit of about 5 to 15, 16, 17, 18, 19, or 20 nucleotides and an upper limit of about 50 to 600 nucleotides, and other particular embodiments are in a size range with a lower limit of about 10 to 20 nucleotides and an upper limit of about 22 to 100 nucleotides. Oligomers may be purified from naturally occurring sources, but may be synthesized by using any well-known enzymatic or chemical method. The term oligonucleotide does not denote any particular function of the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectible moiety (e.g., an acridinium-ester compound). Oligomers may be referred to by a functional name (e.g., capture probe, primer or promoter primer) but those skilled in the art will understand that such terms refer to oligomers.

As used herein, an oligonucleotide "substantially corresponding to" a specified reference nucleic acid sequence means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA or DNA equivalent thereof as well as DNA/RNA chimerics thereof, and includes the complements thereof, unless the context clearly dictates otherwise. This variation from the nucleic acid may be stated in terms of a percentage of identical bases within the sequence or the percentage of perfectly complementary bases between the probe or primer and its target sequence; thus, in certain embodiments, an oligonucleotide "substantially corresponds" to a reference nucleic acid sequence if these percentages of base identity or complementarity are from 100% to about 80%, preferably from 100% to about 85%, or more preferably from 100% to about 90% or from 100% to about 95%. This variation from the nucleic acid may also be stated in terms of the number of nucleobase substitutions in a nucleic acid sequence relative to a reference sequence, or the number of mismatches within a sequence relative to a target sequence; thus, in certain embodiments, an oligonucleotide "substantially corresponds" to a reference nucleic acid sequence if this number of nucleobase substitutions or mismatches is up to four, preferable up to three, or more preferably up to two or up to one substitution(s) or mismatch(es) (i.e., from zero to four, preferably from zero to three, or more preferably from zero to two or from zero to one, inclusive). Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

As used herein, the phrase "or its complement, or an RNA equivalent or DNA/RNA chimeric thereof," with reference to a DNA sequence, includes (in addition to the referenced DNA sequence) the complement of the DNA sequence, an RNA equivalent of the referenced DNA sequence, an RNA equivalent of the complement of the referenced DNA sequence, a DNA/RNA chimeric of the referenced DNA sequence, and a DNA/RNA chimeric of the complement of the referenced DNA sequence. Similarly, the phrase "or its complement, or a DNA equivalent or DNA/RNA chimeric thereof," with reference to an RNA sequence, includes (in addition to the referenced RNA sequence) the complement of the RNA sequence, a DNA equivalent of the referenced RNA sequence, a DNA equivalent of the complement of the referenced RNA sequence, a DNA/RNA chimeric of the referenced RNA sequence, and a DNA/RNA chimeric of the complement of the referenced RNA sequence.

An "amplification oligonucleotide" or "amplification oligomer" is an oligonucleotide that hybridizes to a target nucleic acid, or its complement, and participates in a nucleic acid amplification reaction (e.g., serving as a primer or promoter-primer). Particular amplification oligomers contain at least about 10 contiguous bases, and optionally at least 18, 19, 20, 21, 22, or 23 contiguous bases that are complementary to a region of the target nucleic acid sequence or its complementary strand. The contiguous bases may be at least about 80%, at least about 90%, or completely complementary to the target sequence to which the amplification oligomer binds. One skilled in the art will understand that the recited ranges include all whole and rational numbers within the range (e.g., 92% or 98.377%). Particular amplification oligomers are about 10 to about 60 bases long, or more preferably about 18 to about 26 bases long and optionally may include modified nucleotides.

A "primer" is an oligomer that hybridizes to a template nucleic acid and has a 3' end that is extended by a polymerase enzyme. A primer may be optionally modified, e.g., by including a 5' region that is non-complementary to the target sequence. Such modification can include functional additions, such as tags, promoters, or other non-target-specific sequences used or useful for manipulating or amplifying the primer or target oligonucleotide.

Within the context of transcription-mediated amplification, a primer modified with a 5' promoter sequence is referred to herein as a "promoter-primer." A person of ordinary skill in the art of molecular biology or biochemistry will understand that an oligomer that can function as a primer can be modified to include a 5' promoter sequence and then function as a promoter-primer, and, similarly, any promoter-primer can serve as a primer with or without its 5' promoter sequence. A promoter-primer modified to incorporate a 3' blocked end is referred to herein as a "promoter provider," which is capable of hybridizing to a target nucleic acid and providing an upstream promoter sequence that serves to initiate transcription, but does not provide a primer for oligo extension.

"Non-target-specific sequence" or "non-target-hybridizing sequence" as used herein refers to a region of an oligomer sequence, wherein said region does not stably hybridize with a target sequence under standard hybridization conditions. Oligomers with non-target-specific sequences include, but are not limited to, promoter primers and molecular beacons.

"Nucleic acid amplification" refers to any in vitro procedure that produces multiple copies of a target nucleic acid sequence, or its complementary sequence, or fragments thereof (i.e., an amplified sequence containing less than the complete target nucleic acid). Examples of nucleic acid amplification procedures include transcription associated methods, such as transcription-mediated amplification (TMA), nucleic acid sequence-based amplification (NASBA) and others (e.g., U.S. Pat. Nos. 5,399,491, 5,554, 516, 5,437,990, 5,130,238, 4,868,105, and 5,124,246), replicase-mediated amplification (e.g., U.S. Pat. No. 4,786, 600), the polymerase chain reaction (PCR) (e.g., U.S. Pat. Nos. 4,683,195, 4,683,202, and 4,800,159), ligase chain reaction (LCR) (e.g., EP Patent No. 0320308), helicase-dependent amplification (e.g., U.S. Pat. No. 7,282,328), and strand-displacement amplification (SDA) (e.g., U.S. Pat. No. 5,422,252). Amplification may be linear or exponential. PCR amplification uses DNA polymerase, primers, and thermal cycling steps to synthesize multiple copies of the two complementary strands of DNA or cDNA. LCR amplification uses at least four separate oligonucleotides to amplify a target and its complementary strand by using multiple cycles of hybridization, ligation, and denaturation. Helicase-dependent amplification uses a helicase to separate the two strands of a DNA duplex generating single-stranded templates, followed by hybridization of sequence-specific primers hybridize to the templates and extension by DNA polymerase to amplify the target sequence. SDA uses a primer that contains a recognition site for a restriction endonuclease that will nick one strand of a hemimodified DNA duplex that includes the target sequence, followed by amplification in a series of primer extension and strand displacement steps. Replicase-mediated amplification uses self-replicating RNA molecules, and a replicase such as QB-replicase. Particular embodiments use PCR or TMA, but it will be apparent to persons of ordinary skill in the art that oligomers disclosed herein may be readily used as primers in other amplification methods.

Transcription-associated amplification uses a DNA polymerase, an RNA polymerase, deoxyribonucleoside triphosphates, ribonucleoside triphosphates, a promoter-containing oligonucleotide, and optionally may include other oligonucleotides, to ultimately produce multiple RNA transcripts from a nucleic acid template (described in detail in, e.g., U.S. Pat. Nos. 5,399,491 and 5,554,516 to Kacian et al.; U.S. Pat. No. 5,437,990 to Burg et al.; PCT Publication Nos. WO 88/01302 and WO 88/10315 (Gingeras et al.); U.S. Pat. No. 5,130,238 to Malek et al.; U.S. Pat. Nos. 4,868,105 and 5,124,246 to Urdea et al.; PCT Publication No. WO 94/03472 (McDonough et al.); and PCT Publication No. WO 95/03430 (Ryder et al.)). Methods that use TMA are described in detail previously (e.g., U.S. Pat. Nos. 5,399,491 and 5,554,516).

In cyclic amplification methods that detect amplicons in real-time, the term "Threshold cycle" (Ct) is a measure of the emergence time of a signal associated with amplification of target, and is generally 10× standard deviation of the normalized reporter signal. Once an amplification reaches the "threshold cycle," generally there is considered to be a positive amplification product of a sequence to which the probe binds. The identity of the amplification product can then be determined through methods known to one of skill in the art, such as gel electrophoresis, nucleic acid sequencing, and other such analytical procedures.

By "amplicon" or "amplification product" is meant a nucleic acid molecule generated in a nucleic acid amplification reaction and which is derived from a target nucleic acid. An amplicon or amplification product contains a target nucleic acid sequence that may be of the same or opposite-sense as the target nucleic acid.

As used herein, the term "relative fluorescence unit" ("RFU") is a unit of measurement of fluorescence intensity. RFU varies with the characteristics of the detection means used for the measurement, and can be used as a measurement to compare relative intensities between samples and controls.

"Detection probe oligomer," "detection probe," or "probe" refers to an oligomer that hybridizes specifically to a target sequence, including an amplified sequence, under conditions that promote nucleic acid hybridization, for detection of the target nucleic acid. Detection may either be direct (i.e., probe hybridized directly to the target) or indirect (i.e., a probe hybridized to an intermediate structure that links the probe to the target). Detection probes may be DNA, RNA, analogs thereof or combinations thereof (e.g., DNA/RNA chimerics), and they may be labeled or unlabeled. Detection probes may further include alternative backbone linkages (e.g., 2'-O-methyl linkages). A probe's target sequence generally refers to the specific sequence within a larger sequence which the probe hybridizes specifically. A detection probe may include target-specific sequence(s) and non-target-specific sequence(s). Such non-target-specific sequences can include sequences which will confer a desired secondary or tertiary structure, such as a hairpin structure, which can be used to facilitate detection and/or amplification (see, e.g., U.S. Pat. Nos. 5,118,801, 5,312,728, 6,835,542, and 6,849,412). Probes of a defined sequence may be produced by techniques known to those of ordinary skill in the art, such as by chemical synthesis, and by in vitro or in vivo expression from recombinant nucleic acid molecules.

By "hybridization" or "hybridize" is meant the ability of two completely or partially complementary nucleic acid strands to come together under specified hybridization assay conditions in a parallel or antiparallel orientation to form a stable structure having a double-stranded region. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. See, e.g., R. L. P. Adams et al., *The Biochemistry of the Nucleic Acids* (11th ed. 1992).

By "preferentially hybridize" is meant that under stringent hybridization conditions, an amplification or detection probe oligomer can hybridize to its target nucleic acid to form stable oligomer:target hybrid, but not form a sufficient number of stable oligomer:non-target hybrids. Amplification and detection oligomers that preferentially hybridize to a target nucleic acid are useful to amplify and detect target nucleic acids, but not non-targeted organisms, especially phylogenetically closely related organisms. Thus, the oligomer hybridizes to target nucleic acid to a sufficiently greater extent than to non-target nucleic acid to enable one having ordinary skill in the art to accurately amplify and/or detect the presence (or absence) of nucleic acid derived from the specified target as appropriate. In general, reducing the degree of complementarity between an oligonucleotide sequence and its target sequence will decrease the degree or rate of hybridization of the oligonucleotide to its target region. However, the inclusion of one or more non-complementary nucleosides or nucleobases may facilitate the ability of an oligonucleotide to discriminate against non-target organisms.

Preferential hybridization can be measured using techniques known in the art and described herein, such as in the examples provided below. In some embodiments, there is at least a 10-fold difference between target and non-target hybridization signals in a test sample, at least a 100-fold difference, or at least a 1,000-fold difference. In some embodiments, non-target hybridization signals in a test sample are no more than the background signal level.

By "stringent hybridization conditions," or "stringent conditions" is meant conditions permitting an oligomer to preferentially hybridize to a target nucleic acid and not to nucleic acid derived from a closely related non-target nucleic acid. While the definition of stringent hybridization conditions does not vary, the actual reaction environment that can be used for stringent hybridization may vary depending upon factors including the GC content and length of the oligomer, the degree of similarity between the oligomer sequence and sequences of non-target nucleic acids that may be present in the test sample, and the target sequence. Hybridization conditions include the temperature and the composition of the hybridization reagents or solutions. Exemplary hybridization assay conditions for amplifying and/or detecting target nucleic acids derived from one or more variants of EBV with the oligomers of the present disclosure correspond to a temperature of about 60° C. when the salt concentration, such as a monovalent salt (e.g., KCl, is in the range of about 0.6-0.9 M). Other acceptable stringent hybridization conditions are readily ascertained by those having ordinary skill in the art.

By "assay conditions" is meant conditions permitting stable hybridization of an oligonucleotide to a target nucleic acid. Assay conditions do not require preferential hybridization of the oligonucleotide to the target nucleic acid.

"Label" or "detectable label" refers to a moiety or compound joined directly or indirectly to a probe that is detected or leads to a detectable signal. Direct joining may use covalent bonds or non-covalent interactions (e.g., hydrogen bonding, hydrophobic or ionic interactions, and chelate or coordination complex formation) whereas indirect joining may use a bridging moiety or linker (e.g., via an antibody or additional oligonucleotide(s)). Any detectable moiety may be used, including a radionuclide, a ligand such as biotin or avidin or even a polynucleotide sequence, an enzyme, an enzyme substrate, a reactive group, a chromophore such as a dye or particle (e.g., a latex or metal bead) that imparts a detectable color, a luminescent compound (e.g., bioluminescent, phosphorescent, or a chemiluminescent compound), and a fluorescent compound or moiety (i.e., fluorophore). Embodiments of fluorophores include those that absorb light in the range of about 495 to 650 nm and emit light in the range of about 520 to 670 nm, which include those known as FAM™, TET™, CAL FLUOR™ (Orange or Red), and QUASAR™ compounds. Fluorophores may be used in combination with a quencher molecule that absorbs light when in close proximity to the fluorophore to diminish background fluorescence. Such quenchers are well known in the art and include, for example, BLACK HOLE QUENCHER™ (or BHQ™) or TAMRA™ compounds. Particular embodiments include a "homogeneous detectable label" that is detectable in a homogeneous system in which bound labeled probe in a mixture exhibits a detectable change compared to unbound labeled probe, which allows the label to be detected without physically removing hybridized from unhybridized labeled probe (e.g., U.S. Pat. Nos. 5,283,174, 5,656,207, and 5,658,737). Particular homogeneous detectable labels include chemiluminescent compounds, including acridinium ester ("AE") compounds, such as standard AE or AE derivatives which are well known (U.S. Pat. Nos. 5,656,207, 5,658,737, and 5,639,604). Methods of synthesizing labels, attaching labels to nucleic acid, and detecting signals from labels are well known (e.g., Sambrook et al., *Molecular Cloning, A Laboratory Manual,* 2nd ed. (Cold Spring Harbor Laboratory Press, Cold Spring Harbor, NY, 1989) at Chapt. 10, and U.S. Pat. Nos. 5,658, 737, 5,656,207, 5,547,842, 5,283,174, and 4,581,333, and EP Pat. App. 0 747 706). Particular methods of linking an AE compound to a nucleic acid are known (e.g., U.S. Pat. Nos. 5,585,481 and 5,639,604, see column 10, line 6 to column 11, line 3, and Example 8). Particular AE labeling positions are a probe's central region and near a region of A/T base pairs, at a probe's 3' or 5' terminus, or at or near a mismatch site with a known sequence that is the probe should not detect compared to the desired target sequence. Other detectably labeled probes include TaqMan™ probes, molecular torches, and molecular beacons. TaqMan™ probes include a donor and acceptor label wherein fluorescence is detected upon enzymatically degrading the probe during amplification in order to release the fluorophore from the presence of the quencher. Molecular torches and beacons exist in open and closed configurations wherein the closed configuration quenches the fluorophore and the open position separates the fluorophore from the quencher to allow fluorescence. Hybridization to a target nucleic acid opens the otherwise closed probes.

Sequences are "sufficiently complementary" if they allow stable hybridization of two nucleic acid sequences, e.g., stable hybrids of probe and target sequences, although the sequences need not be completely complementary. That is, a "sufficiently complementary" sequence that hybridizes to another sequence by hydrogen bonding between a subset series of complementary nucleotides by using standard base pairing (e.g., G:C, A:T, or A:U), although the two sequences may contain one or more residues (including abasic positions) that are not complementary so long as the entire sequences in appropriate hybridization conditions to form a stable hybridization complex. Sufficiently complementary sequences may be at least about 80%, at least about 90%, or completely complementary in the sequences that hybridize together. Appropriate hybridization conditions are well-known to those skilled in the art, can be predicted based on sequence composition, or can be determined empirically by using routine testing (e.g., Sambrook et al., *Molecular Cloning, A Laboratory Manual,* $2^{nd}$ ed. at §§ 1.90-1.91, 7.37-7.57, 9.47-9.51 and 11.47-11.57, particularly §§ 9.50-9.51, 11.12-11.13, 11.45-11.47 and 11.55-11.57).

A "non-extendable" oligomer includes a blocking moiety at or near its 3'-terminus to prevent extension. A blocking group near the 3' end is in some embodiments within five residues of the 3' end and is sufficiently large to limit binding of a polymerase to the oligomer, and other embodiments contain a blocking group covalently attached to the 3' terminus. Many different chemical groups may be used to block the 3' end, e.g., alkyl groups, non-nucleotide linkers, alkane-diol dideoxynucleotide residues, and cordycepin. Further examples of blocking moieties include a 3'-deoxy nucleotide (e.g., a 2',3'-dideoxy nucleotide); a 3'-phosphorylated nucleotide; a fluorophore, quencher, or other label that interferes with extension; an inverted nucleotide (e.g., linked to the preceding nucleotide through a 3'-to-3' phosphodiester, optionally with an exposed 5'-OH or phosphate); or a protein or peptide joined to the oligonucleotide so as to prevent further extension of a nascent nucleic acid chain by a polymerase. A non-extendable oligonucleotide of the present disclosure may be at least 10 bases in length, and may be up to 15, 20, 25, 30, 35, 40, 50 or more nucleotides in length. Non-extendable oligonucleotides that comprise a detectable label can be used as probes.

References, particularly in the claims, to "the sequence of SEQ ID NO: X" refer to the base sequence of the corresponding sequence listing entry and do not require identity of the backbone (e.g., RNA, 2'-O-Me RNA, or DNA) or base modifications (e.g., methylation of cytosine residues) unless the context clearly dictates otherwise.

"Sample preparation" refers to any steps or method that treats a sample for subsequent amplification and/or detection of EBV nucleic acids present in the sample. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically capture a target nucleic acid and separate it from other sample components (e.g., as described in U.S. Pat. No. 6,110,678 and International Patent Application Pub. No. WO 2008/016988, each incorporated by reference herein).

"Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. "Separating" or "purifying" does not connote any degree of purification. Typically, separating or purifying removes at least 70%, or at least 80%, or at least 95% of the target nucleic acid from other sample components.

The term "non-linear surfactant," as used herein, means a surfactant having a branched chain structure. A non-linear surfactant may include one or more ring structures, which may be, for example, in a principal chain and/or in one or more branch chains. Exemplary non-linear surfactants include polysorbate 20, polysorbate 40, polysorbate 60, and digitonin. In certain variations, a non-linear surfactant is non-ionic.

The term "specificity," in the context of an amplification and/or detection system, is used herein to refer to the characteristic of the system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio). In terms of detection, specificity generally refers to the ratio of signal produced from target nucleic acids to signal produced from non-target nucleic acids.

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

DETAILED DESCRIPTION

Disclosed herein are compositions, methods, and kits for detecting the nucleic acids of Epstein-Barr virus (EBV). More particularly, there are disclosed oligonucleotide primers and probes that can be used to amplify and detect EBV nucleic acids with high levels of specificity and sensitivity. This was accomplished by sequence selection, and by modification of oligonucleotides to include nucleotide analogs for the purpose of avoiding undesired hybridization reactions.

The present disclosure provides compositions, kits, and methods for amplifying and detecting nucleic acid of Epstein-Barr virus (EBV) in a sample. Preferably, the samples are biological samples obtained from a human subject. The compositions, kits, and methods provide oligonucleotide sequences that recognize target sequences within the EBV genome, including target sequences within the EBV EBNA1 gene, or the complement thereof. Such oligonucleotides may be used as amplification oligonucleotides, which may include primers, promoter primers, blocked oligonucleotides, and promoter provider oligonucleotides, whose functions have been described previously (see, e.g., U.S. Pat. Nos. 4,683,195; 4,683,202; 4,800,159; 5,399,491; 5,554,516; 5,824,518; and 7,374,885; each incorporated by reference herein). Other oligonucleotides may be used as probes for detecting amplified sequences of EBV, or for capture of EBV target nucleic acid.

The methods provide for the sensitive and specific detection of EBV nucleic acids. The methods include performing nucleic acid amplification of an EBV target region and detecting the amplified product by, for example, specifically hybridizing the amplified product with a nucleic acid detection probe that provides a signal to indicate the presence of EBV in the sample. The amplification step includes contacting the sample with one or more amplification oligomers specific for a target sequence in an EBV target nucleic acid to produce an amplified product if EBV nucleic acid is present in the sample. Amplification synthesizes additional copies of the target sequence or its complement by using at least one nucleic acid polymerase and an amplification oligomer to produce the copies from a template strand (e.g., by extending the sequence from a primer using the template strand). One embodiment for detecting the amplified product uses a hybridizing step that includes contacting the amplified product with at least one detection probe oligomer specific for a sequence amplified by the selected amplification oligomers (e.g., a sequence contained in the target sequence flanked by a pair of selected amplification oligomers).

Preferred compositions of the instant disclosure are configured to specifically hybridize to nucleic acid of EBV with minimal cross-reactivity to other, non-EBV nucleic acids suspected of being in a sample (e.g., other viral pathogens). In some aspects, the compositions of the instant disclosure are configured to specifically hybridize to EBV nucleic acid with minimal cross-reactivity to one or more non-EBV pathogens listed in any of Tables 5 and 6. In one aspect, the compositions of the instant disclosure are part of a multiplex system that further includes components and methods of detecting one of more of these non-EBV pathogens. For example, there can be compositions that independently amplify and detect the nucleic acids of EBV and cytomegalovirus (CMV) in the same reaction. Amplified EBV nucleic acids and amplified CMV nucleic acids can be detected using hybridization probes labeled with distinguishable fluorescent labels. In this way, EBV can be detected in the multiplex amplification reaction independent of other target nucleic acids that also may be amplified in the multiplex reaction.

In certain aspects of the disclosure, a composition comprising at least two amplification oligomers is provided for determining the presence or absence of EBV in a sample. Typically, the composition includes at least two amplification oligomers for amplifying a target region of an EBV target nucleic acid corresponding to the sequence of SEQ ID NO:1. In such embodiments, at least one amplification oligomer comprises a target-hybridizing sequence in the sense orientation ("sense THS") and at least one amplification oligomer comprises a target-hybridizing sequence in the antisense orientation ("antisense THS"), where the sense THS and antisense THS are each configured to specifically hybridize to an EBV target sequence corresponding to a sequence contained within SEQ ID NO:1 or the complement thereof, and where the target-hybridizing sequences are selected such that the EBV sequence targeted by antisense THS is situated downstream of the EBV sequence targeted by the sense THS (i.e., the at least two amplification oligomers are situated such that they flank the target region to be amplified). Generally, opposite-strand amplification oligomers useful for synthesizing nucleic acid amplification products are sometimes referred to herein as "first" and "second" amplification oligomers to distinguish one from the other. Alternatively, the opposite-strand amplification oligomers can also be referred to as "forward" and "reverse" amplification oligomers, or forward and reverse "primers" (when the oligomers are extended by a polymerase).

In certain embodiments, the composition is provided as an aqueous or dried formulation for amplification of EBV nucleic acid, or a reaction mixture comprising or reconstituted from such a formulation.

In certain variations, a composition for determining the presence or absence of EBV in a sample further includes at least one detection probe oligomer configured to hybridize to an EBV EBNA1 target sequence that is amplifiable using the first and second amplification oligomers. Preferred EBV EBNA1-specific probes can be 20-25 nucleotides in length, and can include a sequence of bases contained within the sequence of SEQ ID NO:2, or the complement thereof. The probe-hybridizing sequence is flanked by the target-hybridizing sequences of the first and second amplification oligomers. Particularly suitable detection probe oligomers include, for example, oligomers having 22 contiguous bases of SEQ ID NO:2, or the complement thereof, allowing for RNA and DNA equivalent bases, and an RNA equivalent or a DNA/RNA chimeric thereof. One example of a useful probe is given by SEQ ID NO:9. Preferred probes in accordance with the disclosure further include a covalently attached label (i.e., a detectably labeled probe). Highly preferred probes include both a fluorophore moiety and a quencher moiety. A detection probe oligomer optionally includes a 2'-methoxy backbone at one or more linkages in the nucleic acid backbone. In some variations, a composition includes at least two detection probe oligomers. In certain embodiments, a detection probe oligomer is provided in an aqueous or dried (e.g., lyophilized) formulation for detection of EBV nucleic acid, or a reaction mixture that includes such a formulation, or that is reconstituted from such a formulation. Typically, a detection probe oligomer in accordance with the present disclosure further includes a label. Particularly suitable labels include compounds that emit a detectable light signal. Example labels include fluorophores and luminescent (e.g., chemiluminescent) compounds that can be detected in homogeneous assays. More than one label, and more than one type of label, may be present on a particular probe, or detection may rely on using a mixture of probes in which each probe is labeled with a compound that produces a detectable signal (see, e.g., U.S. Pat. Nos. 6,180,340 and 6,350,579, each incorporated by reference herein). Labels may be attached to a probe by various means including covalent linkages, chelation, and ionic interactions. Preferably, the label is covalently attached. For example, in some embodiments, a detection probe has an attached chemiluminescent label such as an acridinium ester (AE) compound (see, e.g., U.S. Pat. Nos. 5,185,439; 5,639,604; 5,585,481; 5,656,744; each incorporated by reference herein). A label, such as a fluorescent or chemiluminescent label, can be attached to the probe by a non-nucleotide linker (see, e.g., U.S. Pat. Nos. 5,585,481; 5,656,744; and 5,639,604, particularly at column 10, line 6 to column 11, line 3, and Example 8; each incorporated by reference herein).

In some embodiments, a probe (e.g., including a fluorescent label) further includes a second label that interacts with the first label. For example, the second label can be a quencher. Detection probes that include both a fluorescent label and a quencher moiety are particularly useful in fluorescence resonance energy transfer (FRET) assays. Specific variations of such detection probes include TaqMan™ detection probes (Roche Molecular Diagnostics), and "molecular beacon" hybridization probes (see Tyagi et al., Nature Biotechnol. 16:49-53, 1998; U.S. Pat. Nos. 5,118,801 and 5,312,728; each incorporated by reference herein). TaqMan™ probes (or similar dual-labeled linear probes including both a fluorescent label and a quencher), can be used in assays where hybridization of the probe to a target or amplicon followed by nucleolysis by a polymerase having 5'-3' exonuclease activity results in liberation of the fluorescent label to result in increased fluorescence, or fluorescence independent of the interaction with the second label.

In some applications, a detection probe exhibiting at least some degree of self-complementarity are used to facilitate detection of probe:target duplexes in a test sample without first requiring the removal of unhybridized probe prior to detection. Specific embodiments of such detection probes include, for example, probes that form conformations held by intramolecular hybridization, such as conformations generally referred to as hairpins. Suitable hairpin probes include a "molecular torch" (see, e.g., U.S. Pat. Nos. 6,849,412; 6,835,542; 6,534,274; and 6,361,945) and a "molecular beacon" (see, e.g., U.S. Pat. Nos. 5,118,801 and 5,312,728). Molecular torches include distinct regions of self-complementarity (coined "the target binding domain" and "the target closing domain") which are connected by a joining region (e.g., a $—(CH_2CH_2O)_3$-linker) and which hybridize to one another under predetermined hybridization assay conditions. When exposed to an appropriate target or denaturing conditions, the two complementary regions (which may be fully or partially complementary) of the molecular torch melt, leaving the target binding domain available for hybridization to a target sequence when the predetermined hybridization assay conditions are restored. Molecular torches are designed so that the target binding domain favors hybridization to the target sequence over the target closing domain. The target binding domain and the target closing domain of a molecular torch include interacting labels (e.g., fluorophore/quencher) positioned so that a different signal is produced when the molecular torch is self-hybridized as opposed to when the molecular torch is hybridized to a target nucleic acid, thereby permitting detection of probe:target duplexes in a test sample in the presence of unhybridized probe having a viable label associated therewith.

In other embodiments, a detection probe is a linear oligomer that does not substantially form conformations maintained by intramolecular bonds. In specific variations, a linear detection probe oligomer includes a chemiluminescent compound as the label (e.g., an acridinium ester (AE) compound). In other embodiments, a linear detection probe oligomer includes a fluorophore as the label. In some embodiments of a linear detection probe oligomer including a fluorophore, the oligomer further includes a quenching moiety (e.g., a TaqMan probe).

Examples of interacting donor/acceptor label pairs that may be used in connection with the disclosure, making no attempt to distinguish FRET from non-FRET pairs, include fluorescein/tetramethylrhodamine, IAEDANS/fluorescein, EDANS/DABCYL, coumarin/DABCYL, fluorescein/ fluorescein, BODIPY FL/BODIPY FL, fluorescein/ DABCYL, lucifer yellow/DABCYL, BODIPY/DABCYL, eosin/DABCYL, erythrosine/DABCYL, tetramethylrhodamine/DABCYL, Texas Red/DABCYL, CY5/BH1, CY5/ BH2, CY3/BH1, CY3/BH2 and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. Non-fluorescent acceptors such as DABCYL and the QSY7 dyes advantageously eliminate the potential problem of background fluorescence resulting from direct (i.e., non-sensitized) acceptor excitation. Exemplary fluorophore moieties that can be used as one member of a donor-acceptor pair include fluorescein, ROX, and the CY dyes (such as CY5). Exemplary quencher moieties that can be used as another member of a donor-acceptor pair include DABCYL and the BLACK HOLE QUENCHER moieties which are available from Biosearch Technologies, Inc., (Novato, Calif.).

In some embodiments, a labeled oligomer (e.g., a detection probe) is non-extendable. For example, the labeled oligomer can be rendered non-extendable by 3'-phosphorylation, having a 3'-terminal 3'-deoxynucleotide (e.g., a terminal 2',3'-dideoxynucleotide), having a 3'-terminal inverted nucleotide (e.g., in which the last nucleotide is inverted such that it is joined to the penultimate nucleotide by a 3' to 3' phosphodiester linkage or analog thereof, such as a phosphorothioate), or having an attached fluorophore, quencher, or other label that interferes with extension (possibly but not necessarily attached via the 3' position of the terminal nucleotide). In some embodiments, the 3'-terminal nucleotide is not methylated.

Also provided by the present disclosure are compositions that include one or more detection probe oligomers as described herein.

In some aspects, the present disclosure provides methods utilizing an oligomer or oligomer combination as described herein. Any method disclosed herein is also to be understood as a disclosure of corresponding uses of materials involved in the method directed to accomplish the purpose of the method. Any of the oligomers that include an EBV EBNA1-target-hybridizing sequence and any combinations (e.g., kits and compositions) including such an oligomer are to be understood as also being disclosed for use in detecting or quantifying EBV, and for use in the preparation of a composition for detecting or quantifying EBV.

Broadly speaking, methods may include one or more of the following components: target capture, in which EBV nucleic acid (e.g., from a sample, such as a clinical sample) is annealed to a capture oligomer; isolation (e.g., washing, to remove material not associated with a capture oligomer); amplification; and amplicon detection (e.g., amplicon quantification, which may be performed in real time with amplification). Certain embodiments involve each of the foregoing steps. Certain embodiments involve exponential amplification, optionally with a preceding linear amplification step. Certain embodiments involve exponential amplification and amplicon detection. Certain embodiments involve any two of the components listed above. Certain embodiments involve any two components listed adjacently above (e.g., washing and amplification, or amplification and detection).

In some embodiments, the present disclosure provides a method for determining the presence or absence of EBV in a sample using an oligomer combination as described herein. Such a method generally includes (1) contacting the sample with at least two amplification oligomers for amplifying an EBV EBNA1 nucleic acid target region; (2) performing an in vitro nucleic acid amplification reaction using the amplification oligomers to generate an amplification product; and (3) detecting the presence or absence of the amplification product, thereby determining the presence or absence of EBV in the sample.

A detection method in accordance with the present disclosure typically further includes the step of obtaining the sample to be contacted with the at least two amplification oligomers. In certain embodiments, "obtaining" a sample to be used in steps (1)-(3) includes, for example, receiving the sample at a testing facility or other location where one or more steps of the method are performed, and/or retrieving the sample from a location (e.g., from storage or other depository) within a facility where one or more steps of the method are performed.

Amplifying an EBV target sequence can employ an in vitro amplification reaction using at least two amplification oligomers that flank a target region to be amplified. In particular embodiments, the target region to be amplified is an EBV EBNA1 target region contained within the sequence of SEQ ID NO:1 or the complement thereof. Particularly suitable oligomer combinations for amplifying the target region are described herein. For example, in some embodiments, an amplification oligomer combination for amplifying an EBV EBNA1 target region includes first and second amplification oligomers including, respectively, (A) a first EBV EBNA1-specific target-hybridizing sequence of 18-25 nucleotides in length, more preferably 20-25 nucleotides in length, where the target-hybridizing sequence is fully contained within the sequence of SEQ ID NO:3 or an RNA equivalent or a DNA/RNA chimeric thereof, and (B) a second EBV EBNA1-specific target-hybridizing sequence of 18-25 nucleotides in length, more preferably 20-21 nucleotides in length, where the target-hybridizing sequence is fully contained within the sequence of SEQ ID NO:4 or an RNA equivalent or a DNA/RNA chimeric thereof. In some embodiments, an amplification oligomer combination for amplifying an EBV target region includes first and second EBV EBNA1-specific amplification oligomers including, respectively, (A) a first EBV EBNA1-specific target-hybridizing sequence that is either SEQ ID NO:5 or a sequence substantially corresponding to SEQ ID NO:5, or an RNA equivalent or a DNA/RNA chimeric thereof, or SEQ ID NO:6 or a sequence substantially corresponding to SEQ ID NO:6, or an RNA equivalent or a DNA/RNA chimeric thereof; and (B) a second EBV EBNA1-specific target-hybridizing sequence that is either SEQ ID NO:7 or a sequence substantially corresponding to SEQ ID NO:7, or an RNA equivalent or a DNA/RNA chimeric thereof, or SEQ ID NO:8 or a sequence substantially corresponding to SEQ ID NO:8, or an RNA equivalent or a DNA/RNA chimeric thereof.

A detection method in accordance with the present disclosure can further include the step of obtaining the sample to be subjected to subsequent steps of the method. In certain embodiments, "obtaining" a sample to be used includes, for example, receiving the sample at a testing facility or other location where one or more steps of the method are performed, and/or retrieving the sample from a location (e.g., from storage or other depository) within a facility where one or more steps of the method are performed.

In certain embodiments, the method further includes purifying the EBV target nucleic acid from other components in the sample (e.g., using a capture step prior to performing a nucleic acid amplification step). Such purification may include methods of separating nucleic acids contained in a sample from other sample components, or removing or degrading non-nucleic acid sample components (e.g., protein, carbohydrate, salt, lipid, etc). In some embodiments, DNA in the sample is degraded (e.g., with DNase), and optionally removing or inactivating the DNase or removing degraded DNA. In some other embodiments, RNA in the sample is degraded (e.g., by treatment under alkaline conditions that hydrolyze RNA).

In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains EBV nucleic acid and other sample components.

Optionally, target capture can occur in a solution phase mixture that contains one or more capture probe oligomers that hybridize to the EBV target sequence under hybridizing conditions. For embodiments wherein the capture probe includes a capture probe tail, the EBV-target:capture-probe complex can be captured by adjusting the hybridization conditions so that the capture probe tail hybridizes to an immobilized probe. Optionally, EBV nucleic acid can be captured onto a solid support using hybridization approaches that are substantially independent of the target sequence. Certain embodiments use a particulate solid support, such as paramagnetic beads.

Isolation of nucleic acids can follow capture, where, for example, the complex on the solid support is separated from other sample components. Isolation can be accomplished by any appropriate technique (e.g., washing a support associated with the EBV target-sequence one or more times) to remove other sample components and/or unbound oligomer. In embodiments using a particulate solid support, such as paramagnetic beads, particles associated with the EBV target may be suspended in a washing solution and retrieved from the washing solution, in some embodiments by using magnetic attraction. To limit the number of handling steps, the isolated target nucleic acid may be amplified by simply mixing the target sequence in the complex on the support with amplification oligomers and proceeding with amplification steps.

Exponentially amplifying an EBV target sequence can utilize an in vitro amplification reaction employing at least two amplification oligomers that flank a target region to be amplified. In some embodiments, at least first and second oligomers as described herein are provided. The amplification reaction can be either temperature-cycled or isothermal. Suitable amplification methods include, for example, the polymerase chain reaction (PCR), replicase-mediated amplification, ligase chain reaction (LCR), strand-displacement amplification (SDA), and transcription-mediated or transcription-associated amplification (TMA).

A detection step may be performed using any of a variety of known techniques to detect a signal specifically associated with the amplified target sequence. This can include hybridizing the amplification product with a labeled detection probe and detecting a signal resulting from the labeled probe, including from label released from the probe following hybridization in some embodiments. In some embodiments, the labeled probe includes a second moiety, such as a quencher or other moiety that interacts with the first label, as discussed above. The detection step may also provide additional information on the amplified sequence (e.g., all or a portion of its nucleic acid base sequence). Detection may be performed after the amplification reaction is completed, or may be performed simultaneously with amplifying the target region (e.g., using a real-time format). In one embodiment, the detection step allows homogeneous detection (e.g., detection of the hybridized probe without removal of unhybridized probe from the mixture), for example as disclosed in U.S. Pat. Nos. 5,639,604 and 5,283,174. In some embodiments, the association of nucleic acids with a surface results in a physical change that can be detected as an optical change or an electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481; each incorporated by reference herein). Directly or indirectly labeled probes that specifically associate with the amplified product provide a detectable signal that indicates the presence of the target nucleic acid in the sample. In particular, the amplified product will contain a target sequence in or complementary to a sequence in the EBV EBNA1 gene, and a probe will bind directly or indirectly to a sequence contained in the amplified product to indicate the presence of EBV nucleic acid in the tested sample.

In embodiments that detect the amplified product near or at the end of the amplification step, a linear detection probe may be used to provide a signal to indicate hybridization of the probe to the amplified product. One example of such detection uses a luminescently labeled probe that hybridizes to a target nucleic acid. The luminescent label is then hydrolyzed from non-hybridized probe. Detection can be performed by measuring chemiluminescence using a luminometer. (See, e.g., International Patent Application Pub. No. WO 89/002476, incorporated by reference herein). In other embodiments employing real-time detection, the detection probe may be a hairpin probe such as, for example, a molecular beacon, molecular torch, or hybridization switch probe that is labeled with a reporter moiety that is detected when the probe binds to amplified product (e.g., a dual-labeled hairpin probe including both a fluorescent label and a quenching moiety). In still other embodiments employing real-time detection, the detection probe is a linear oligomer such as an oligomer labeled with both a fluorophore and a quenching moiety (e.g., a TaqMan probe). Such probes may include target-hybridizing sequences and non-target-hybridizing sequences. Various forms of such probes have been described previously (see, e.g., U.S. Pat. Nos. 5,210,015; 5,487,972; 5,118,801; 5,312,728; 5,925,517; 6,150,097; 6,849,412; 6,835,542; 6,534,274; and 6,361,945; and US Patent Application Pub. Nos. 20060068417A1 and 20060194240A1; each incorporated by reference herein).

Assays for detection of the EBV nucleic acid may optionally include a non-EBV internal control (IC) nucleic acid that is amplified and detected in the same assay reaction mixtures by using amplification and detection oligomers specific for the IC sequence. The IC nucleic acid can be, for example, a DNA plasmid, an RNA template sequence (e.g., an in vitro transcript), or a synthetic nucleic acid that is spiked into a sample. Alternatively, the IC nucleic acid sequence may be a cellular component, which may be from exogenous cellular sources or endogenous cellular sources relative to the specimen. In these instances, an internal control nucleic acid can be co-amplified with the EBV nucleic acid in the amplification reaction mixtures. The internal control amplification product and the EBV target sequence amplification product can be detected independently. This can be accomplished using different target-specific hybridization probes (e.g., dual labeled hybridization probes), each being labeled with a distinguishable fluorophore.

In certain embodiments, amplification and detection of a signal from an amplified IC sequence demonstrates that the assay reagents, conditions, and performance of assay steps were properly used in the assay if no signal is obtained for the intended target EBV nucleic acid (e.g., samples that test negative for EBV). An IC may also be used as an internal calibrator for the assay when a quantitative result is desired. For example, the signal obtained from the IC amplification and detection can be used to set a parameter used in an algorithm for quantitating the amount of EBV nucleic acid in a sample based on the signal obtained for an amplified EBV target sequence. ICs are also useful for monitoring the integrity of one or more steps in an assay. The primers and probe for the IC target sequence are configured and synthesized by using any well-known method provided that the primers and probe function for amplification of the IC target sequence and detection of the amplified IC sequence using substantially the same assay conditions used to amplify and detect the EBV target sequence. In preferred embodiments that include a target capture-based purification step, it is preferred that a target capture probe specific for the IC target be included in the assay in the target capture step so that the IC is treated in the assay in a manner analogous to that for the intended EBV analyte in all of the assay steps.

Also provided herein are formulations for determining the presence or absence of EBV in a sample. In some embodiments, a formulation is an aqueous formulation including (1) at least two EBV EBNA1-specific amplification oligomers for amplification of an EBV target region as described herein, and (2) a pH buffer. An aqueous formulation for amplification of an EBV nucleic acid may include one or more additional components such as a DNA polymerase enzyme, a reverse transcriptase enzyme, or a detection probe oligomer. In some embodiments, a formulation is an aqueous formulation including (1) an EBV EBNA1 detection probe oligomer as described herein, and (2) a pH buffer. An aqueous formulation including one or more detection probe oligomers may include one or more additional components, such as a surfactant, a DNA polymerase enzyme, a reverse transcriptase enzyme, or at least one amplification oligomer. Particularly suitable surfactants include, for example, polyethylene glycol mono [4-(1,1,3,3-tetramethylbutyl) phenyl] ether and polyoxyethylene sorbitan fatty acid esters (e.g., polysorbate 20, polysorbate 40, or polysorbate 60). In some embodiments, a surfactant in an aqueous detection probe formulation is a non-linear surfactant such as, for example, a polyoxyethylene sorbitan fatty acid ester (e.g., polysorbate 20, polysorbate 40, or polysorbate 60) or digitonin. An aqueous formulation as above for amplification or detection of EBV nucleic acid may further include a bulking agent, such as trehalose, raffinose, or a combination thereof. In some embodiments, an aqueous formulation as above contains an inorganic salt such as a magnesium salt, a potassium salt, or a sodium salt. In some variations, the concentration of the inorganic salt is 4 mM or less. A particularly suitable pH buffer for an aqueous formulation as above is Tris (2-amino-2-(hydroxymethyl)-1,3-propanediol).

In a related aspect, for long-term storage, an aqueous formulation as described herein may be aliquoted into vials, ampules, or other containers and dried (e.g., lyophilized) according to procedures known in the art. The dried product typically appears as a powder or cake. The containers are then sealed. Methods of preparing such dried formulations from the aqueous formulation, as well as the dried formulations prepared by such methods, are additional aspects of the present disclosure. In yet another aspect, the present disclosure provides a dried formulation that enables reconstitution into an aqueous formulation as described herein. Dried formulations for amplification or detection of EBV nucleic acid typically contain, in addition to one or more amplification oligomers and/or detection probes as described herein, a bulking agent such as trehalose, raffinose, or a combination thereof. In some embodiments that further include an inorganic salt, the percent mass of the inorganic salt to the mass of the dried formulation is 0.30% or less, 0.25% or less, or 0.20% or less. Methods of preparing a dried formulation from a lyophilized formulation as described herein are also encompassed by the present disclosure. Such methods generally include dissolving the dried formulation in a suitable diluent (e.g., an aqueous pH buffer or water) to provide a reconstituted formulation.

Also provided by the subject disclosure is a reaction mixture for determining the presence or absence of an EBV target nucleic acid in a sample. A reaction mixture in accordance with the present disclosure includes one or both of (1) an oligomer combination as described herein for amplification of an EBV EBNA1 target nucleic acid, and (2) one or more detection probe oligomers as described herein for determining the presence or absence of an EBV EBNA1 amplification product. The reaction mixture may further include a number of optional components such as, for example, capture probes (e.g., poly-(k) capture probes as described in US 2013/0209992, which is incorporated herein by reference). For an amplification reaction mixture, the reaction mixture will typically include other reagents suitable for performing in vitro amplification such as buffers, salt solutions, appropriate nucleotide triphosphates (e.g., dATP, dCTP, dGTP, and dTTP; and/or ATP, CTP, GTP and UTP), and/or enzymes (e.g., a thermostable DNA polymerase, or reverse transcriptase and/or RNA polymerase), and will typically include test sample components in which an EBV target nucleic acid may or may not be present. A reaction mixture may include amplification oligomers for only one target region of an EBV genome, or it may include amplification oligomers for multiple EBV target regions. In addition, for a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture). In some embodiments, a reaction mixture includes an aqueous formulation as described above. In some embodiments, a reaction mixture is reconstituted from a dried formulation using water, or an aqueous solution optionally including a pH buffer.

Also provided are kits for practicing the methods as described herein. A kit in accordance with the present disclosure include a packaged combination of one or both of (1) an oligomer combination as described herein for amplification of an EBV target nucleic acid, and (2) one or more detection probe oligomers as described herein for determining the presence or absence of an EBV amplification product. In some embodiments, any oligomer combination described herein is present in the kit. The kits may further include a number of optional components such as, for example, capture probes (e.g., poly-(k) capture probes as described in US 2013/0209992). Other reagents that may be present in the kits include reagents suitable for performing in vitro amplification such as buffers, salt solutions, appropriate nucleotide triphosphates (e.g., dATP, dCTP, dGTP, dTTP; and/or ATP, CTP, GTP and UTP), and/or enzymes (e.g., a thermostable DNA polymerase, or a reverse transcriptase and/or RNA polymerase). Oligomers as described herein can be packaged in a variety of different embodiments, and those skilled in the art will appreciate that the disclosure embraces many different kit configurations. For example, a kit optionally can include amplification oligomers for only one target region of an EBV genome, or it may include amplification oligomers for multiple EBV target regions. In addition, for a kit that includes a detection probe together with an amplification oligomer combination, selection of amplification oligomers and detection probe oligomers for a kit are linked by a common target region (i.e., the kit will include a probe that binds to a sequence amplifiable by an amplification oligomer combination of the kit). In certain embodiments, the kit further includes a set of instructions for practicing methods in accordance with the present disclosure, where the instructions may be associated with a package insert and/or the packaging of the kit or the components thereof.

Primers of the disclosure can be used to amplify nucleic acids (e.g., DNA) of the EBV genome in in vitro nucleic acid amplification assays. Any of several in vitro nucleic acid amplification systems can be employed for this purpose. Particularly described below are experimental procedures demonstrating amplification by the polymerase chain reaction (PCR), where detection of amplification products took place as the amplification reaction was occurring. This is sometimes referred to as "real-time PCR," or more generally as "real-time amplification and detection." In alternative embodiments, real-time PCR can be carried out using a hydrolysis probe (i.e., a probe that is digested by the nuclease activity of a DNA polymerase, such as Taq DNA polymerase), a molecular beacon, a molecular torch, and the like.

The disclosed oligonucleotide reagents can be used for molecular diagnostic and screening assays. Preferred primer and probe combination have EBV detection or reactivity rates of at least 95% when the amplification and detection reaction contains 50 copies of EBV target DNA per reaction. This was demonstrated for multiple EBV strains. The formulation of primers and probes does not cross-react with common organisms potentially found in human blood (e.g., serum and plasma). Optionally, the primers and probe of the disclosure can function in the presence of primers and a probe that amplify and detect the EBV target sequence, without interference or cross-reactivity with a DNA internal control nucleic acid. The probes that detect nucleic acids of EBV and the internal control are labeled with fluorophores that can be detected independent of each other (e.g., in different "channels" of a detection apparatus). As well, the primers and probe used for detecting EBV can be used in a multiplex assay that also detects CMV without cross-reactivity or interference. Preferably, probes for detecting EBV and CMV in multiplex assays are also labeled with distinguishable fluorophores. Advantageously, the preferred primer and probe combination for detecting EBV can detect nucleic acids of EBV in the presence of organisms commonly found in plasma and serum.

Template Sequences, and Primer and Probe Domains

Various amplification and detection oligonucleotides for an EBV target nucleic acid sequence were prepared and evaluated during development of the disclosed technique. All oligonucleotide designs targeted the EBNA1 gene of the EBV genome. Sets of oligonucleotides were tested for the ability to amplify and detect a target sequence region contained within the sequence of SEQ ID NO:1.

The sequences of nucleic acid amplification products in accordance with the disclosure preferably include sequences that are contained entirely within the sequence of SEQ ID NO:1, or the complement thereof. The sequence of SEQ ID NO:1 contains sequence domains from which forward primers and probes can be derived. More particularly, forward primers for amplifying EBV sequences can include target-hybridizing sequences of 18 to 25 contiguous bases, or more preferably 20 to 25 contiguous bases of SEQ ID NO:3. Optionally, forward primers are 18 to 25 nucleotides in length, more preferably 20 to 25 nucleotides in length. For example, forward primers can be 18 nucleotides in length, 19 nucleotides in length, 20 nucleotides in length, 21 nucleotides in length, 22 nucleotides in length, 23 nucleotides in length, 24 nucleotides in length, or 25 nucleotides in length. Reverse primers useful in combination with one or more forward primers can include target-hybridizing sequences of 18 to 25 contiguous bases, or more preferably 20 to 21 contiguous bases of SEQ ID NO:4, which is contained within and complementary to the sequence of SEQ ID NO:1. For example, reverse primers can be 18 nucleotides in length, 19 nucleotides in length, 20 nucleotides in length, 21 nucleotides in length, 22 nucleotides in length, 23 nucleotides in length, 24 nucleotides in length, or 25 nucleotides in length. Optionally, probes useful for detecting amplification products synthesized using the forward and reverse primers can be up to 30 nucleotides in length. More preferably, the probes are up to 26 nucleotides in length, still more preferably up to 23 nucleotides in length, and yet still more preferably up to 22 nucleotides in length. Probes can include at least 18 contiguous nucleotides, more preferably 20-26 contiguous nucleotides, more preferably 24 contiguous nucleotides, still more preferably 23 contiguous nucleotides, or yet still more preferably 22 contiguous nucleotides of SEQ ID NO:2. Detectably labeled probe oligonucleotides were configured to (e.g., by selection of length and/or by incorporation of nucleotide analogs) have melting temperatures (Tms) higher than the Tm of the same strand primer (i.e., the forward primer in this Example). This arrangement ensured probe binding at a temperature higher than the temperature at which primer binding and extension took place during the PCR temperature cycling routine.

Optionally, probes for detecting nucleic acid amplification products can include a fluorophore moiety and/or a quencher moiety.

Table 1 lists the sequences of probes designed for use in detecting EBV nucleic acid amplification products. Optionally, amplification products to be detected can be synthesized using opposite-sense amplification oligonucleotides from within SEQ ID NO:3 and SEQ ID NO:4, together with an EBV template polynucleotide having the sequence given by SEQ ID NO:1. All sequences listed in Table 1 represent contiguous nucleotides contained within the sequence of SEQ ID NO:2. Optionally, oligonucleotides having any of the tabulated sequences can be joined to a detectable label moiety (e.g., a fluorophore). Preferably, oligonucleotides having the indicated sequences can be joined to paired sets of interactive labels (e.g., a fluorophore moiety and a quencher moiety). All probes having nucleotide base sequences shown in Table 1, together with the complements thereof, are embraced by the disclosure. Working Examples presented below used the probe of SEQ ID NO:9 for illustrative purposes.

TABLE 1

Detection Probe Oligomer Sequences

| SEQ ID NO: | Sequence |
|---|---|
| 9 | CCGTGTATTCCCCCGCACTAAA |
| 10 | CCGTGTATTCCCCCGCACTAAAG |
| 11 | CCGTGTATTCCCCCGCACTAAAGA |
| 12 | GCCGTGTATTCCCCCGCACTAAA |
| 13 | AGCCGTGTATTCCCCCGCACTAAA |
| 14 | GCCGTGTATTCCCCCGCACTAAAG |
| 15 | AGCCGTGTATTCCCCCGCACTAAAG |
| 16 | GCCGTGTATTCCCCCGCACTAAAGA |
| 17 | AGCCGTGTATTCCCCCGCACTAAAGA |
| 18 | CCGTGTATTCCCCCGCACTAA |
| 19 | CCGTGTATTCCCCCGCACTA |
| 20 | CGTGTATTCCCCCGCACTAAA |
| 21 | GTGTATTCCCCCGCACTAAA |
| 22 | GTGTATTCCCCCGCACTA |
| 23 | TCCCCAGTAGACATCATGCGTGC |
| 24 | TCCCCAGTAGACATCATGCGTG |
| 25 | CCCCAGTAGACATCATGCGTGC |
| 26 | CCCCAGTAGACATCATGCGTG |
| 27 | TCCCCAGTAGACATCATGCGT |
| 28 | CCCAGTAGACATCATGCGTGC |
| 29 | CCCAGTAGACATCATGCGTG |
| 30 | CCCCAGTAGACATCATGCGT |
| 31 | CCCAGTAGACATCATGCGT |

Example 1 describes procedures used for testing certain oligonucleotides from within the specified sequence domains (i.e., primer and probe combinations) to illustrate detection of nucleic acid sequences in the EBNA1 coding region of EBV. A cloned plasmid harboring the ENBA1 target sequence that served as the template in this procedure. Amplification and detection were performed using a real-time PCR protocol. An internal control nucleic acid was coamplified and detected independently to validate any negative results.

Example 1

Amplification and Detection of EBV Nucleic Acid in the Region Encoding EBNA1

Paired sets of primers were combined with a probe in real-time PCR reactions primed with a cloned plasmid template containing the EBNA1 target region. Forward primers had the sequences of SEQ ID NO:5 and SEQ ID NO:6. Reverse primers had the sequences of SEQ ID NO:7 and SEQ ID NO:8. All reactions included one each of the forward and reverse primers. A single probe from within the sequence of SEQ ID NO:2 had the sequence of SEQ ID NO:9.

PCR reaction mixtures included the thermostable Taq DNA polymerase and reagents (e.g., nucleotides, salts, cofactors, etc.) necessary for amplicon synthesis, as will be familiar to those having an ordinary level of skill in the art. Template nucleic acids included the sequences of SEQ ID NO:1 or an internal control sequence that was unrelated to the EBNA1 target sequence. All trials included primers and a labeled hydrolysis probe specific for the internal control amplicon. The EBV-specific probe was labeled with Cal Fluor Orange 560 fluorescent moiety at its 5'-end, and with a Black Hole Quencher 1 moiety at its 3'-end. Combinations of individual forward and reverse primers were tested in the amplification reactions, where amplification products were detected using the hydrolysis probe of SEQ ID NO:9. The EBV template was included at levels of 10 copies/reaction, 100 copies/reaction, and 1,000 copies/reaction for each tested primer combination. The amplification routine began with a 2 minute step at 95° C. to denature nucleic acids. This was followed by 45 cycles at 60° C. for 0.25 minutes, and at 95° C. for 0.08 minutes. The appearance of EBV-specific amplicons was monitored by accumulation of fluorescent signal in the HEX channel of a monitoring fluorometer, where loss of fluorescence quenching indicated Taq-dependent cleavage of the labeled hydrolysis probe. Fluorescence was monitored as a function of cycle number.

Table 2 summarizes results of the real-time PCR procedure, where the results were assessed using a collection of metrics for each different oligonucleotide set. These metrics included: RFU range ratio, signal-to-noise ratio, RFU range, slope of the fluorescent run curve at the time of static threshold crossing ("Tslope"), and the Ct value for the reaction that included 1,000 copies of the EBV template nucleic acid. The RFU range ratio was calculated by dividing the fluorescent RFU (relative fluorescence units) at the 100 copy/reaction level by the RFU range at the 1,000 copy/reaction level. All metrics except for Ct were taken from the 100 copy/reaction trial data. As will be apparent from the tabulated information, the labeled probe functioned well in all trials. All primer combinations used in this demonstration also gave good results. It was noted, however, that the combinations of primers identified by SEQ ID NO:5 and SEQ ID NO:7, and by SEQ ID NO:5 and SEQ ID NO:8 gave particularly good results with respect to all measures shown in the table.

TABLE 2

Oligonucleotide Scoring Results

| Oligo Primer Combination | RFU range ratio | signal-to-noise ratio | RFU range (RFU) | Tslope (RFU/cycle) | Ct at 1,000 copies/reaction (cycles) |
|---|---|---|---|---|---|
| SEQ ID NO: 5 SEQ ID NO: 7 | 0.83 | 13 | 14,202 | 44 | 29.1 |
| SEQ ID NO: 5 SEQ ID NO: 8 | 0.83 | 13 | 13,184 | 39 | 29.0 |
| SEQ ID NO: 6 SEQ ID NO: 7 | 0.84 | 12 | 13,323 | 38 | 29.3 |
| SEQ ID NO: 6 SEQ ID NO: 8 | 0.73 | 12 | 11,360 | 39 | 30.0 |

Example 2 describes procedures that demonstrated sensitivity and linearity using selected oligonucleotide reagents from Example 1.

Example 2

EBV Target Nucleic Acid Sensitivity

Sensitivity was first evaluated by testing an EBV plasmid clone harboring the EBNA1 target region of SEQ ID NO:1 in a specimen transport medium (STM) at 3 concentrations (5 to 500 copies/reaction). STM is a phosphate-buffered (pH 6.6 to pH 6.8) solution that includes 3% (w/v) lithium lauryl sulfate. In addition to promoting lysis of any cells that may be present, STM protects nucleic acids by inhibiting the activity of nuclease enzymes that may be present in the sample. PCR formulations included the EBV primers of SEQ ID NO:5 and SEQ ID NO:7, and the probe of SEQ ID NO:9. For sensitivity testing, carried out using replicates of 30. The plasmid clone was spiked into STM at the indicated concentrations and tested with 3 probe lots. For linearity testing, amplification reactions were carried out using replicates of 6, with the plasmid being spiked into STM at the indicated concentrations and tested with 1 probe lot. All specimens were processed using an automated instrument to isolate nucleic acids by target capture, and then amplify the isolated nucleic acids using a real-time PCR protocol.

Results of the procedure are summarized in Table 3. In this procedure, "reactivity" was indicated when the fluorescence magnitude crossed a static threshold set at 500 RFU. 100% detection of the EBV plasmid was observed down to 10 copies/reaction.

Example 3 describes procedures that established levels of sensitivity for detection of EBV in different matrices.

Example 3

Viral Sensitivity

EBV reference strain B95-8 in pooled plasma, pooled serum, and STM was evaluated for reactivity with a PCR formulation that included the template sequence of SEQ ID NO:1, the primers of SEQ ID NO:5 and SEQ ID NO:7, and the probe of SEQ ID NO:9. Briefly, EBV virus strain B95-8 was spiked into each matrix at the indicated concentrations. The specimens in plasma and serum were diluted 1:0.2 with PBS containing 3 mg/ml proteinase K (PK) enzyme and 50 ng/µl of an additional target capture oligo (TCO) that permitted capture of nucleic acids from solution phase onto solid support beads in a manner substantially independent of target nucleotide sequence. Neither PK nor extra TCO were added to the STM samples. All trials were carried out in replicates of 20. As in Example 2, all specimens were processed using an automated instrument to isolate nucleic acids by target capture, and then amplify the isolated nucleic acids using a real-time PCR protocol.

Results from the procedure are summarized in Table 4. Again, "reactivity" was indicated when the magnitude of the fluorescence reading crossed a static threshold set at 500 RFU. 95% detection was observed for EBV spiked in STM at 100 copies/ml. 100% detection was observed at 1,000 copies/ml in serum and 316 copies/ml in plasma. Isolating and amplifying nucleic acids from blood products reduced sensitivity of detection only slightly. Thus, the real-time assay for detecting EBV can be used for detecting EBV using nucleic acids isolated from blood products. This can involve use of an automated instrument that isolates nucleic acids by target capture, and then amplifies the isolated nucleic acids using a real-time PCR protocol.

TABLE 3

Plasmid Sensitivity and Linearity Results

| Study | Plasmid conc. (copies/reaction) | Reactivity | Avg. RFU | Avg. TSlope | Avg. Baseline (RFU) | Avg. Ct | Signal to noise |
|---|---|---|---|---|---|---|---|
| Plasmid Sensitivity | 5 | 97% | 13,838 | 304 | 1,379 | 36.2 | 10.7 |
|  | 50 | 100% | 20,364 | 314 | 1,320 | 32.7 | 16.4 |
|  | 500 | 100% | 24,736 | 349 | 1,266 | 29.3 | 20.6 |
| Plasmid Linearity | 10 | 100% | 11,663 | 319 | 1,622 | 35.4 | 8.2 |
|  | 18 | 100% | 11,656 | 323 | 1,579 | 35.1 | 8.4 |
|  | 1,800 | 100% | 23,783 | 401 | 1,539 | 28.1 | 16.4 |
|  | 180,000 | 100% | 27,399 | 387 | 1,368 | 21.1 | 21.1 |

TABLE 4

Viral Sensitivity Testing Results

| Matrix | Conc. of initial specimen (cp/ml) | Reactivity | Avg Ct | Avg RFU | Avg TSlope | Avg Baseline (RFU) | Avg Total RFU | Avg Signal to Noise |
|---|---|---|---|---|---|---|---|---|
| Plasma | 31.6 | 30% | 37.4 | 6,975 | 303 | 1,742 | 3,835 | 2.3 |
|  | 100 | 55% | 38.0 | 6,158 | 297 | 1,843 | 5,229 | 2.8 |
|  | 316 | 100% | 34.3 | 11,917 | 315 | 1,863 | 13,779 | 7.4 |
|  | 1000 | 100% | 33.3 | 14,440 | 343 | 1,928 | 16,368 | 8.5 |
| Serum | 31.6 | 55% | 36.9 | 6,546 | 301 | 1,959 | 5,560 | 2.8 |
|  | 100 | 75% | 36.3 | 7517 | 307 | 1,875 | 7,513 | 4.0 |
|  | 316 | 90% | 36.4 | 9525 | 317 | 1,802 | 10,374 | 5.8 |
|  | 1000 | 100% | 34.3 | 13840 | 337 | 1,821 | 15,661 | 8.6 |
| STM | 3.16 | 20% | 37.1 | 2321 | 312 | 1,654 | 3,131 | 1.9 |
|  | 10 | 65% | 37.9 | 4838 | 272 | 1,629 | 5,741 | 3.5 |
|  | 31.6 | 70% | 37.2 | 8069 | 297 | 1,634 | 8,807 | 5.4 |
|  | 100 | 95% | 35.5 | 12767 | 306 | 1,597 | 13,726 | 8.6 |
|  | 316 | 100% | 33.4 | 17157 | 315 | 1,609 | 18,766 | 11.6. |

Example 4 describes procedures illustrating specificity of the EBV real-time assay by demonstrating lack of detection of a range of organisms potentially found in human blood. The procedure verified that 35 different organisms were not detected by the EBV assay.

Example 4

EBV Assay is Highly Specific

A collection of organisms commonly found in human blood was prepared in 9 panels by spiking about $1 \times 10^4$ to about $1 \times 10^6$ organisms/ml into STM. Each panel was evaluated for specificity with a PCR formulation that included the template sequence of SEQ ID NO:1, the primers of SEQ ID NO:5 and SEQ ID NO:7, and the probe of SEQ ID NO:9.

Table 5 summarizes the panel composition and reactivity results from the procedure. None of the tested organisms yielded a positive result for EBV, but IC was detected in all trials (i.e., thereby confirming that all trials were functionally reactive). The positive control trial was positive for detection of EBV and IC, and the negative control was positive for detection of IC only. Taken together, the results confirmed that the amplification and detection system was specific for EBV, and did not detect nucleic acids from other organisms.

TABLE 5

Specificity Testing Results

| Panel | Organism | Strain | Reactivity |
|---|---|---|---|
| 1 | BK Virus | N/A | 0/3 = 0% |
|  | Cytomegalovirus (CMV) | RC256 |  |
|  | Human Parvovirus | B19 |  |
|  | Varicella Zoster Virus (VZV) | Isolate A |  |
| 2 | Candida albicans | CBS 562 | 0/3 = 0% |
|  | Chlamydia trachomatis | Serovar E |  |
|  | Human Immunodeficiency virus Type 1 (HIV-1) | Type B |  |
|  | Hepatitis A virus (HAV) | HM175 |  |
| 3 | Dengue Virus Type 1 | Hawaii | 0/3 = 0% |
|  | Dengue Virus Type 2 | New Guinea C |  |
|  | Dengue Virus Type 3 | H87 |  |
|  | Dengue Virus Type 4 | H241 |  |
| 4 | Herpes Simplex Virus Type 2 (HSV-2) | MS | 0/3 = 0% |
|  | HIV Type 2 (HIV-2) | NIH-Z |  |
|  | HPV purified plasmid DNA | Type 18 |  |
|  | Synthetic HPV DNA | Type 16 |  |

TABLE 5-continued

Specificity Testing Results

| Panel | Organism | Strain | Reactivity |
|---|---|---|---|
| 5 | Human Herpes Virus Type 6A (HHV-6A) | GS | 0/3 = 0% |
|  | Human Herpes Virus Type 6B (HHV-6B) | Z29 |  |
|  | Human Herpes Virus Type 7 (HHV-7) | SB |  |
|  | Human Herpes Virus Type 8 (HHV-8) | N/A |  |
| 6 | Human T-Lymphotropic Virus Type I (HTLV-I) | N/A | 0/3 = 0% |
|  | Human T-Lymphotropic Virus Type II (HTLV-II) Culture Fluid | N/A |  |
|  | Human Hepatitis B Virus (HBV) | N/A |  |
|  | Human Hepatitis C Virus (HCV) | N/A |  |
| 7 | Mycobacterium smegmatis | W-113 | 0/3 = 0% |
|  | Neisseria gonorrhoeae | NCTC 8375 |  |
|  | Propionibacterium acnes | NCTC 737 |  |
|  | Staphylococcus aureus | NCTC 8532 |  |
| 8 | West Nile Virus (WNV) | NY 2001-6263 | 0/3 = 0% |
|  | Vaccinia Virus | "Vaccine" |  |
|  | Trichomonas vaginalis | JH 31A #4 |  |
|  | Staphylococcus epidermidis | RP62A |  |
|  | HSV-1 Strain MacIntyre | MacIntyre |  |
|  | Mycobacterium gordonae | L. Wayne W-1609 |  |
| 9 | Human PBMC | N/A | 0/6 = 0% |

Example 5 describes the procedures that demonstrated efficient detection of EBV without interference by any of a number of test organisms.

Example 5

Interference Testing

EBV reactivity was evaluated in the presence of 35 organisms from the specificity study, and also in the presence of human peripheral blood mononuclear cells. Briefly, panels 2-8 from the specificity study were diluted 1:10 in STM, and EBV (Strain: B95-8) was spiked into the samples at 27,778 copies/ml. Panel 1 was prepared fresh in STM. An additional panel containing peripheral blood mononuclear cells at $5 \times 10^4$ cells/ml was tested. Both panels had EBV spiked in at 27,778 copies/ml. BK was also spiked into each panel to evaluate BK interference at 27,778 copies/ml. Each panel was evaluated for EBV performance in the presence of 4-5 commonly found organisms with a PCR formulation that included the template sequence of SEQ ID NO:1, the primers of SEQ ID NO:5 and SEQ ID NO:7, and the probe of SEQ ID NO:9.

Table 6 presents reactivity results obtained using various panel compositions. Results were compared to a positive control consisting of EBV at 27,778 copies/ml in STM. EBV was detected in 100% of the panels with no more than a 2.0 Ct difference when compared to the positive control. The internal control was detected in 100% of the panels. The positive control trial was positive for EBV and IC and the negative control trial was positive for IC only. Thus, there was no evidence that any of the tested organisms interfered with detection of EBV using the indicated combination of probe and primers.

TABLE 6

EBV Performance In the Presence of Common Organisms

| Pane 1 | Organism | Strain | Final Concentration | Units | Reactivity |
|---|---|---|---|---|---|
| 1 | CMV | RC256 | $1.43 \times 10^5$ | copies/ml | |
| | Human Parvovirus | B19 | $1.00 \times 10^5$ | IU/ml | |
| | Varicella Zoster Virus (VZV) | Isolate A | $1.00 \times 10^6$ | IU/ml | |
| 2 | *Candida albicans* | CBS 562 | $1.00 \times 10^5$ | CFU/ml | 1/1 = 100% |
| | *Chlamydia trachomatis* | Serovar E | $1.00 \times 10^5$ | IFU/ml | |
| | Human Immunodeficiency virus Type 1 (HIV-1) | Type B | $1.00 \times 10^4$ | copies/ml | |
| | Hepatitis A virus (HAV) | HM175 | $1.43 \times 10^4$ | TCID50/ml | |
| 3 | Dengue Virus Type 1 | Hawaii | $1.43 \times 10^3$ | TCID50/ml | 1/1 = 100% |
| | Dengue Virus Type 2 | New Guinea C | $1.43 \times 10^3$ | TCID50/ml | |
| | Dengue Virus Type 3 | H87 | $1.43 \times 10^4$ | TCID50/ml | |
| | Dengue Virus Type 4 | H241 | $1.43 \times 10^3$ | TCID50/ml | |
| 4 | Herpes Simplex Virus Type 2 (HSV-2) | MS | $1.43 \times 10^3$ | TCID50/ml | 1/1 = 100% |
| | HIV Type 2 (HIV-2) | NIH-Z | $1.43 \times 10^2$ | TCID50/ml | |
| | HPV purified plasmid DNA | Type 18 | $1.00 \times 10^5$ | copies/ml | |
| | Synthetic HPV DNA | Type 16 | $1.00 \times 10^3$ | copies/ml | |
| 5 | Human Herpes Virus Type 6A (HHV-6A) | GS | $1.00 \times 10^5$ | copies/ml | 1/1 = 100% |
| | Human Herpes Virus Type 6B (HHV-6B) | Z29 | $1.00 \times 10^5$ | copies/ml | |
| | Human Herpes Virus Type 7 (HHV-7) | SB | $1.43 \times 10^5$ | TCID50/ml | |
| | Human Herpes Virus Type 8 (HHV-8) | N/A | $1.00 \times 10^5$ | copies/ml | |
| 6 | Human T-Lymphotropic Virus Type I (HTLV-I) | N/A | $1.00 \times 10^5$ | vp/ml | 1/1 = 100% |
| | Human T-Lymphotropic Virus Type II (HTLV-II) Culture Fluid | N/A | $1.00 \times 10^5$ | vp/ml | |
| | Human Hepatitis B Virus (HBV) | N/A | $1.00 \times 10^3$ | copies/ml | |
| | Human Hepatitis C Virus (HCV) | N/A | $1.00 \times 10^3$ | copies/ml | |
| 7 | *Mycobacterium smegmatis* | W-113 | $1.00 \times 10^5$ | CFU/ml | 1/1 = 100% |
| | *Neisseria gonorrhoeae* | NCTC 8375 | $1.00 \times 10^5$ | CFU/ml | |
| | *Propionibacterium acnes* | NCTC 737 | $1.00 \times 10^5$ | CFU/ml | |
| | *Staphylococcus aureus* | NCTC 8532 | $1.00 \times 10^5$ | CFU/ml | |
| 8 | West Nile Virus (WNV) | NY 2001-6263 | $5.00 \times 10^2$ | copies/ml | 1/1 = 100% |
| | Vaccinia Virus | "Vaccine" | $1.43 \times 10^5$ | TCID50/ml | |
| | Trichomonas vaginalis | JH 31A #4 | $1.00 \times 10^5$ | cells/ml | |
| | *Staphylococcus epidermidis* | RP62A | $1.00 \times 10^5$ | CFU/ml | |
| | HSV-1 Strain MacIntyre | MacIntyre | $5.00 \times 10^3$ | TCID50/ml | |
| | *Mycobacterium gordonae* | L. Wayne W-1609 | $1.00 \times 10^5$ | copies/ml | |
| 9 | PBMC | N/A | $5.00 \times 10^4$ | Cells/ml | 1/1 = 100% |

All of the compositions, kits, and methods disclosed and claimed herein can be made and executed without undue experimentation in light of the present disclosure. While the disclosure describes preferred embodiments, it will be apparent to those of skill in the art that variations may be applied without departing from the spirit and scope of the disclosure. All such variations and equivalents apparent to those skilled in the art, whether now existing or later developed, are deemed to be within the spirit and scope of the disclosure.

All patents, patent applications, and publications mentioned in the specification are indicative of the levels of those of ordinary skill in the art to which the disclosure pertains. All patents, patent applications, and publications are herein incorporated by reference in their entirety for all purposes and to the same extent as if each individual publication was specifically and individually indicated to be incorporated by reference in its entirety for any and all purposes.

What is claimed is:

1. A reaction mixture for determining the presence or absence of Epstein-Barr virus (EBV) in a sample, said reaction mixture comprising:
   a detection probe oligomer for detecting EBV nucleic acids,
      wherein the detection probe oligomer is up to 30 nucleotides in length and comprises the base sequence of SEQ ID NO:22 or the complement thereof, allowing for substitution of RNA and DNA equivalent bases; and
   a pair of amplification oligomers,
      wherein a first amplification oligomer of the pair comprises 18-25 contiguous bases of SEQ ID NO:3, allowing for substitution of RNA and DNA equivalent bases, and
      wherein a second amplification oligomer of the pair comprises 18-25 contiguous bases of SEQ ID NO:4, allowing for substitution of RNA and DNA equivalent bases.

2. The reaction mixture of claim 1, wherein the detection probe oligomer further comprises a detectable label.

3. The reaction mixture of claim 2, wherein the detectable label comprises an interactive label pair comprising a fluorophore moiety and a quencher moiety.

4. The reaction mixture of claim 1, wherein each of the first and second amplification oligomers is up to 25 nucleotides in length.

5. The reaction mixture of claim 4, wherein the base sequence of the first amplification oligomer is either SEQ ID NO:5 or SEQ ID NO:6, and wherein the base sequence of the second amplification oligomer is either SEQ ID NO:7 or SEQ ID NO:8.

6. The reaction mixture of claim 5, wherein the base sequence of the first amplification oligomer is SEQ ID NO:5.

7. The reaction mixture of claim 6, wherein the base sequence of the second amplification oligomer is SEQ ID NO:7.

8. The reaction mixture of claim 5, wherein the base sequence of the second amplification oligomer is SEQ ID NO:7.

9. The reaction mixture of claim 1, wherein the first amplification oligomer is 20 nucleotides in length, and wherein the base sequence of the first amplification oligomer consists of 20 contiguous bases of SEQ ID NO:3.

10. The reaction mixture of claim 9, wherein the base sequence of the first amplification oligomer is SEQ ID NO:5.

11. The reaction mixture of claim 1, wherein the second amplification oligomer is 20 nucleotides in length, and wherein the base sequence of the second amplification oligomer consists of 20 contiguous bases of SEQ ID NO:4.

12. The reaction mixture of claim 11, wherein the base sequence of the second amplification oligomer is SEQ ID NO:7.

13. The reaction mixture of claim 1, wherein the detection probe oligomer is 22 nucleotides in length and comprises the base sequence of SEQ ID NO:9.

14. A method of determining the presence or absence of Epstein-Barr virus (EBV) in a sample, said method comprising the steps of:

(a) contacting a sample to be tested for the presence of EBV with an oligomer combination that comprises,
 a first amplification oligomer that comprises 18-25 contiguous bases of SEQ ID NO:3, allowing for substitution of RNA and DNA equivalent bases,
 a second amplification oligomer that comprises 18-25 contiguous bases of SEQ ID NO:4, allowing for substitution of RNA and DNA equivalent bases, and
 a detection probe oligomer of up to 30 nucleotides in length that comprises the base sequence of SEQ ID NO:22 or the complement thereof, allowing for substitution of RNA and DNA equivalent bases;
(b) performing an in vitro nucleic acid amplification reaction using the oligomer combination, wherein any EBV target nucleic acid, if present in the sample, is a template for generating an amplification product; and
(c) detecting, with the detection probe oligomer, the presence or absence of the amplification product, thereby determining the presence or absence of EBV in the sample.

15. The method of claim 14, wherein the detection probe oligomer further comprises a detectable label.

16. The method of claim 15, wherein the detectable label of the detection probe oligomer comprises an interactive label pair comprising a fluorophore moiety and a quencher moiety.

17. The method of claim 16, wherein the in vitro nucleic acid amplification reaction in step (b) is a multiplex in vitro nucleic acid amplification reaction that amplifies and detects, in addition to any nucleic acid of EBV that may be present in the sample, any nucleic acid of cytomegalovirus (CMV) that may be present in the sample.

18. The method of claim 14, wherein the sample comprises nucleic acids isolated from any of human blood, human plasma, or human serum.

19. The method of claim 14, wherein the in vitro nucleic acid amplification reaction comprises Taq DNA polymerase.

20. The method of claim 14, wherein steps (b) and (c) take place concurrently, the in vitro nucleic acid amplification reaction being a real-time nucleic acid amplification reaction.

21. The method of claim 20, wherein the in vitro nucleic acid amplification reaction in step (b) is a PCR amplification reaction that comprises a DNA polymerase with a 5' to 3' exonuclease activity.

22. The method of claim 14, wherein before step (a) there is the step of isolating nucleic acids, and wherein all of the steps are performed using a single automated instrument.

23. The method of claim 14, wherein the detection probe oligomer is 22 nucleotides in length and comprises the base sequence of SEQ ID NO:9.

24. A kit of reagents, comprising in one or more vials:
 a detection probe oligomer for detecting Epstein-Barr virus (EBV) nucleic acids,
  wherein the detection probe oligomer is up to 30 nucleotides in length and comprises the base sequence of SEQ ID NO:22 or the complement thereof, allowing for substitution of RNA and DNA equivalent bases; and
 a pair of amplification oligomers,
  wherein a first amplification oligomer of the pair comprises 18-25 contiguous bases of SEQ ID NO:3, allowing for substitution of RNA and DNA equivalent bases, and
  wherein a second amplification oligomer of the pair comprises 18-25 contiguous bases of SEQ ID NO:4, allowing for substitution of RNA and DNA equivalent bases.

25. The kit of claim 24, wherein the detection probe oligomer further comprises a detectable label.

26. The kit of claim 25, wherein the detectable label of the detection probe oligomer comprises an interactive label pair comprising a fluorophore moiety and a quencher moiety.

27. The kit of claim 24, wherein each of the first and second amplification oligomers is up to 25 nucleotides in length.

28. The kit of claim 27, wherein the base sequence of the first amplification oligomer is either SEQ ID NO:5 or SEQ ID NO:6, and wherein the base sequence of the second amplification oligomer is either SEQ ID NO:7 or SEQ ID NO:8.

29. The kit of claim 28, wherein the base sequence of the first amplification oligomer is SEQ ID NO:5.

30. The kit of claim 29, wherein the base sequence of the second amplification oligomer is SEQ ID NO:7.

31. The kit of claim 28, wherein the base sequence of the second amplification oligomer is SEQ ID NO:7.

32. The kit of claim 24, wherein the first amplification oligomer is 20 nucleotides in length, and wherein the base sequence of the first amplification oligomer consists of 20 contiguous bases of SEQ ID NO:3.

33. The kit of claim 32, wherein the base sequence of the first amplification oligomer is SEQ ID NO:5.

34. The kit of claim 24, wherein the second amplification oligomer is 20 nucleotides in length, and wherein the base sequence of the second amplification oligomer consists of 20 contiguous bases of SEQ ID NO:4.

35. The kit of claim 34, wherein the base sequence of the second amplification oligomer is SEQ ID NO:7.

36. The kit of claim 24, wherein the first and second amplification oligomers are packaged together in one vial, and wherein the probe oligonucleotide is packaged in a separate vial.

37. The kit of claim 24, wherein the detection probe oligomer is 22 nucleotides in length and comprises the base sequence of SEQ ID NO:9.

38. A detection probe oligomer for detecting Epstein-Barr virus (EBV) nucleic acids, wherein the detection probe oligomer is up to 30 nucleotides in length and comprises the base sequence of SEQ ID NO:9 or the complement thereof, allowing for substitution of RNA and DNA equivalent bases, wherein positions 1, 2, 10-14, 16, and 18 of SEQ ID NO:9 are 5-methyl cytosines.

39. The detection probe oligomer of claim 38, further comprising a detectable label.

40. The detection probe oligomer of claim 39, wherein the detectable label comprises an interactive label pair comprising a fluorophore moiety and a quencher moiety.

41. The detection probe oligomer of claim 40, wherein the detection probe oligomer is 22 nucleotides in length with a base sequence consisting of SEQ ID NO:9.

42. The detection probe oligomer of claim 40, wherein the detection probe oligomer is a dual-labeled hydrolysis probe.

43. The detection probe oligomer of claim 38, wherein the probe is hybridized to a complementary nucleic acid strand in the presence of a DNA polymerase that comprises a 5' to 3' exonuclease activity.

44. The detection probe oligomer of claim 38, wherein the detection probe oligomer is 22 nucleotides in length.

* * * * *

```
                               SEQUENCE LISTING

<160> NUMBER OF SEQ ID NOS: 31

<210> SEQ ID NO 1
   <211> LENGTH: 172
   <212> TYPE: DNA
   <213> ORGANISM: Human herpesvirus 4
   <220> FEATURE:
   <221> NAME/KEY: misc_feature
   <222> LOCATION: (1)..(172)
   <223> OTHER INFORMATION: Target nucleic acid sequence

<400> SEQUENCE: 1
atgtaactta tgtaacttgt taggagacgc cctcaatcgt attaaaagcc gtgtattccc       60
ccgcactaaa gaataaatcc ccagtagaca tcatgcgtgc tgttggtgta tttctggcca      120
tctgtcttgt caccattttc gtcctcccaa catggggcaa ttgggcatac cc              172

<210> SEQ ID NO 2
   <211> LENGTH: 54
   <212> TYPE: DNA
   <213> ORGANISM: Human herpesvirus 4
   <220> FEATURE:
   <221> NAME/KEY: misc_feature
   <222> LOCATION: (1)..(54)
   <223> OTHER INFORMATION: EBV EBNA1 probe domain

<400> SEQUENCE: 2
agccgtgtat tcccccgcac taaagaataa atccccagta gacatcatgc gtgc             54

<210> SEQ ID NO 3
   <211> LENGTH: 37
   <212> TYPE: DNA
   <213> ORGANISM: Human herpesvirus 4
   <220> FEATURE:
   <221> NAME/KEY: misc_feature
   <222> LOCATION: (1)..(37)
   <223> OTHER INFORMATION: Amplification oligomer domain

<400> SEQUENCE: 3
atgtaacttg ttaggagacg ccctcaatcg tattaaa                                37

<210> SEQ ID NO 4
   <211> LENGTH: 72
   <212> TYPE: DNA
   <213> ORGANISM: Human herpesvirus 4
   <220> FEATURE:
   <221> NAME/KEY: misc_feature
   <222> LOCATION: (1)..(72)
   <223> OTHER INFORMATION: Amplification oligomer domain

<400> SEQUENCE: 4
gggtatgccc aattgcccca tgttgggagg acgaaaatgg tgacaagaca gatggccaga       60
aatacaccaa ca                                                           72

<210> SEQ ID NO 5
```

```
<211> LENGTH: 20
<212> TYPE: DNA
<213> ORGANISM: Human herpesvirus 4
<220> FEATURE:
<221> NAME/KEY: misc_feature
<222> LOCATION: (1)..(20)
<223> OTHER INFORMATION: Amplification oligomer

<400> SEQUENCE: 5
ttaggagacg ccctcaatcg                                           20

<210> SEQ ID NO 6
<211> LENGTH: 25
<212> TYPE: DNA
<213> ORGANISM: Human herpesvirus 4
<220> FEATURE:
<221> NAME/KEY: misc_feature
<222> LOCATION: (1)..(25)
<223> OTHER INFORMATION: Amplification Oligomer

<400> SEQUENCE: 6
ttaggagacg ccctcaatcg tatta                                     25

<210> SEQ ID NO 7
<211> LENGTH: 20
<212> TYPE: DNA
<213> ORGANISM: Human herpesvirus 4
<220> FEATURE:
<221> NAME/KEY: misc_feature
<222> LOCATION: (1)..(20)
<223> OTHER INFORMATION: Amplification oligomer
<220> FEATURE:
<221> NAME/KEY: misc_feature
<222> LOCATION: (4)..(4)
<223> OTHER INFORMATION: Base position occupied by 5-methylcytosine
<220> FEATURE:
<221> NAME/KEY: misc_feature
<222> LOCATION: (5)..(5)
<223> OTHER INFORMATION: Base position occupied by 5-methylcytosine
<220> FEATURE:
<221> NAME/KEY: misc_feature
<222> LOCATION: (13)..(13)
<223> OTHER INFORMATION: Base position occupied by 5-methylcytosine
<220> FEATURE:
<221> NAME/KEY: misc_feature
<222> LOCATION: (15)..(15)
<223> OTHER INFORMATION: Base position occupied by 5-methylcytosine
<220> FEATURE:
<221> NAME/KEY: misc_feature
<222> LOCATION: (16)..(16)
<223> OTHER INFORMATION: Base position occupied by 5-methylcytosine
<220> FEATURE:
<221> NAME/KEY: misc_feature
<222> LOCATION: (19)..(19)
<223> OTHER INFORMATION: Base position occupied by 5-methylcytosine

<400> SEQUENCE: 7
tggccagaaa tacaccaaca                                           20

<210> SEQ ID NO 8
<211> LENGTH: 21
<212> TYPE: DNA
<213> ORGANISM: Human herpesvirus 4
<220> FEATURE:
<221> NAME/KEY: misc_feature
<222> LOCATION: (1)..(21)
<223> OTHER INFORMATION: Amplification oligomer

<400> SEQUENCE: 8
aattgcccca tgttgggagg a                                         21
```

```
<210> SEQ ID NO 9
<211> LENGTH: 22
<212> TYPE: DNA
<213> ORGANISM: Human herpesvirus 4
<220> FEATURE:
<221> NAME/KEY: misc_feature
<222> LOCATION: (1)..(22)
<223> OTHER INFORMATION: Probe sequence
<220> FEATURE:
<221> NAME/KEY: misc_feature
<222> LOCATION: (1)..(1)
<223> OTHER INFORMATION: Base position occupied by 5-methylcytosine
<220> FEATURE:
<221> NAME/KEY: misc_feature
<222> LOCATION: (2)..(2)
<223> OTHER INFORMATION: Base position occupied by 5-methylcytosine
<220> FEATURE:
<221> NAME/KEY: misc_feature
<222> LOCATION: (10)..(10)
<223> OTHER INFORMATION: Base position occupied by 5-methylcytosine
<220> FEATURE:
<221> NAME/KEY: misc_feature
<222> LOCATION: (11)..(11)
<223> OTHER INFORMATION: Base position occupied by 5-methylcytosine
<220> FEATURE:
<221> NAME/KEY: misc_feature
<222> LOCATION: (12)..(12)
<223> OTHER INFORMATION: Base position occupied by 5-methylcytosine
<220> FEATURE:
<221> NAME/KEY: misc_feature
<222> LOCATION: (13)..(13)
<223> OTHER INFORMATION: Base position occupied by 5-methylcytosine
<220> FEATURE:
<221> NAME/KEY: misc_feature
<222> LOCATION: (14)..(14)
<223> OTHER INFORMATION: Base position occupied by 5-methylcytosine
<220> FEATURE:
<221> NAME/KEY: misc_feature
<222> LOCATION: (16)..(16)
<223> OTHER INFORMATION: Base position occupied by 5-methylcytosine
<220> FEATURE:
<221> NAME/KEY: misc_feature
<222> LOCATION: (18)..(18)
<223> OTHER INFORMATION: Base position occupied by 5-methylcytosine

<400> SEQUENCE: 9
ccgtgtattc ccccgcacta aa                                              22

<210> SEQ ID NO 10
<211> LENGTH: 23
<212> TYPE: DNA
<213> ORGANISM: Human herpesvirus 4
<220> FEATURE:
<221> NAME/KEY: misc_feature
<222> LOCATION: (1)..(23)
<223> OTHER INFORMATION: Probe sequence

<400> SEQUENCE: 10
ccgtgtattc ccccgcacta aag                                             23

<210> SEQ ID NO 11
<211> LENGTH: 24
<212> TYPE: DNA
<213> ORGANISM: Human herpesvirus 4
<220> FEATURE:
<221> NAME/KEY: misc_feature
<222> LOCATION: (1)..(24)
<223> OTHER INFORMATION: Probe sequence

<400> SEQUENCE: 11
ccgtgtattc ccccgcacta aaga                                            24

<210> SEQ ID NO 12
```

```
<211> LENGTH: 23
<212> TYPE: DNA
<213> ORGANISM: Human herpesvirus 4
<220> FEATURE:
<221> NAME/KEY: misc_feature
<222> LOCATION: (1)..(23)
<223> OTHER INFORMATION: Probe sequence

<400> SEQUENCE: 12
gccgtgtatt cccccgcact aaa                                          23

<210> SEQ ID NO 13
<211> LENGTH: 24
<212> TYPE: DNA
<213> ORGANISM: Human herpesvirus 4
<220> FEATURE:
<221> NAME/KEY: misc_feature
<222> LOCATION: (1)..(24)
<223> OTHER INFORMATION: Probe sequence

<400> SEQUENCE: 13
agccgtgtat tccccccgcac taaa                                        24

<210> SEQ ID NO 14
<211> LENGTH: 24
<212> TYPE: DNA
<213> ORGANISM: Human herpesvirus 4
<220> FEATURE:
<221> NAME/KEY: misc_feature
<222> LOCATION: (1)..(24)
<223> OTHER INFORMATION: Probe sequence

<400> SEQUENCE: 14
gccgtgtatt cccccgcact aaag                                         24

<210> SEQ ID NO 15
<211> LENGTH: 25
<212> TYPE: DNA
<213> ORGANISM: Human herpesvirus 4
<220> FEATURE:
<221> NAME/KEY: misc_feature
<222> LOCATION: (1)..(25)
<223> OTHER INFORMATION: Probe sequence

<400> SEQUENCE: 15
agccgtgtat tccccccgcac taaag                                       25

<210> SEQ ID NO 16
<211> LENGTH: 25
<212> TYPE: DNA
<213> ORGANISM: Human herpesvirus 4
<220> FEATURE:
<221> NAME/KEY: misc_feature
<222> LOCATION: (1)..(25)
<223> OTHER INFORMATION: Probe sequence

<400> SEQUENCE: 16
gccgtgtatt cccccgcact aaaga                                        25

<210> SEQ ID NO 17
<211> LENGTH: 26
<212> TYPE: DNA
<213> ORGANISM: Human herpesvirus 4
<220> FEATURE:
<221> NAME/KEY: misc_feature
<222> LOCATION: (1)..(26)
<223> OTHER INFORMATION: Probe sequence

<400> SEQUENCE: 17
```

```
agccgtgtat tcccccgcac taaaga                                              26
```

<210> SEQ ID NO 18
<211> LENGTH: 21
<212> TYPE: DNA
<213> ORGANISM: Human herpesvirus 4
<220> FEATURE:
<221> NAME/KEY: misc_feature
<222> LOCATION: (1)..(21)
<223> OTHER INFORMATION: Probe sequence

<400> SEQUENCE: 18

```
ccgtgtattc ccccgcacta a                                                   21
```

<210> SEQ ID NO 19
<211> LENGTH: 20
<212> TYPE: DNA
<213> ORGANISM: Human herpesvirus 4
<220> FEATURE:
<221> NAME/KEY: misc_feature
<222> LOCATION: (1)..(20)
<223> OTHER INFORMATION: Probe sequence

<400> SEQUENCE: 19

```
ccgtgtattc ccccgcacta                                                     20
```

<210> SEQ ID NO 20
<211> LENGTH: 21
<212> TYPE: DNA
<213> ORGANISM: Human herpesvirus 4
<220> FEATURE:
<221> NAME/KEY: misc_feature
<222> LOCATION: (1)..(21)
<223> OTHER INFORMATION: Probe sequence

<400> SEQUENCE: 20

```
cgtgtattcc cccgcactaa a                                                   21
```

<210> SEQ ID NO 21
<211> LENGTH: 20
<212> TYPE: DNA
<213> ORGANISM: Human herpesvirus 4
<220> FEATURE:
<221> NAME/KEY: misc_feature
<222> LOCATION: (1)..(20)
<223> OTHER INFORMATION: Probe sequence

<400> SEQUENCE: 21

```
gtgtattccc ccgcactaaa                                                     20
```

<210> SEQ ID NO 22
<211> LENGTH: 18
<212> TYPE: DNA
<213> ORGANISM: Human herpesvirus 4
<220> FEATURE:
<221> NAME/KEY: misc_feature
<222> LOCATION: (1)..(18)
<223> OTHER INFORMATION: Probe sequence

<400> SEQUENCE: 22

```
gtgtattccc ccgcacta                                                       18
```

<210> SEQ ID NO 23
<211> LENGTH: 23
<212> TYPE: DNA
<213> ORGANISM: Human herpesvirus 4
<220> FEATURE:

```
<221> NAME/KEY: misc_feature
<222> LOCATION: (1)..(23)
<223> OTHER INFORMATION: Probe sequence

<400> SEQUENCE: 23
tccccagtag acatcatgcg tgc                                              23

<210> SEQ ID NO 24
<211> LENGTH: 22
<212> TYPE: DNA
<213> ORGANISM: Human herpesvirus 4
<220> FEATURE:
<221> NAME/KEY: misc_feature
<222> LOCATION: (1)..(22)
<223> OTHER INFORMATION: Probe sequence

<400> SEQUENCE: 24
tccccagtag acatcatgcg tg                                               22

<210> SEQ ID NO 25
<211> LENGTH: 22
<212> TYPE: DNA
<213> ORGANISM: Human herpesvirus 4
<220> FEATURE:
<221> NAME/KEY: misc_feature
<222> LOCATION: (1)..(22)
<223> OTHER INFORMATION: Probe sequence

<400> SEQUENCE: 25
ccccagtaga catcatgcgt gc                                               22

<210> SEQ ID NO 26
<211> LENGTH: 21
<212> TYPE: DNA
<213> ORGANISM: Human herpesvirus 4
<220> FEATURE:
<221> NAME/KEY: misc_feature
<222> LOCATION: (1)..(21)
<223> OTHER INFORMATION: Probe sequence

<400> SEQUENCE: 26
ccccagtaga catcatgcgt g                                                21

<210> SEQ ID NO 27
<211> LENGTH: 21
<212> TYPE: DNA
<213> ORGANISM: Human herpesvirus 4
<220> FEATURE:
<221> NAME/KEY: misc_feature
<222> LOCATION: (1)..(21)
<223> OTHER INFORMATION: Probe sequence

<400> SEQUENCE: 27
tccccagtag acatcatgcg t                                                21

<210> SEQ ID NO 28
<211> LENGTH: 21
<212> TYPE: DNA
<213> ORGANISM: Human herpesvirus 4
<220> FEATURE:
<221> NAME/KEY: misc_feature
<222> LOCATION: (1)..(21)
<223> OTHER INFORMATION: Probe sequence

<400> SEQUENCE: 28
cccagtagac atcatgcgtg c                                                21
```

```
<210> SEQ ID NO 29
<211> LENGTH: 20
<212> TYPE: DNA
<213> ORGANISM: Human herpesvirus 4
<220> FEATURE:
<221> NAME/KEY: misc_feature
<222> LOCATION: (1)..(20)
<223> OTHER INFORMATION: Probe sequence

<400> SEQUENCE: 29
cccagtagac atcatgcgtg                                           20

<210> SEQ ID NO 30
<211> LENGTH: 20
<212> TYPE: DNA
<213> ORGANISM: Human herpesvirus 4
<220> FEATURE:
<221> NAME/KEY: misc_feature
<222> LOCATION: (1)..(20)
<223> OTHER INFORMATION: Probe sequence

<400> SEQUENCE: 30
ccccagtaga catcatgcgt                                           20

<210> SEQ ID NO 31
<211> LENGTH: 19
<212> TYPE: DNA
<213> ORGANISM: Human herpesvirus 4
<220> FEATURE:
<221> NAME/KEY: misc_feature
<222> LOCATION: (1)..(19)
<223> OTHER INFORMATION: Probe sequence

<400> SEQUENCE: 31
cccagtagac atcatgcgt                                            19
```